(12) United States Patent
Vertegaal et al.

(10) Patent No.: US 7,809,160 B2
(45) Date of Patent: Oct. 5, 2010

(54) METHOD AND APPARATUS FOR CALIBRATION-FREE EYE TRACKING USING MULTIPLE GLINTS OR SURFACE REFLECTIONS

(75) Inventors: Roel Vertegaal, Battersea (CA); Changuk Sohn, Kingston (CA); Daniel Cheng, Kingston (CA); Victor Macfarlane, Battersea (CA); Jeffrey S. Shell, Toronto (CA)

(73) Assignee: Queen's University at Kingston, Kingston, Ontario (CA)

( * ) Notice: Subject to any disclaimer, the term of this patent is extended or adjusted under 35 U.S.C. 154(b) by 1025 days.

(21) Appl. No.: 10/987,299

(22) Filed: Nov. 15, 2004

(65) Prior Publication Data

US 2005/0175218 A1   Aug. 11, 2005

Related U.S. Application Data

(60) Provisional application No. 60/519,608, filed on Nov. 14, 2003, provisional application No. 60/564,615, filed on Apr. 23, 2004.

(51) Int. Cl.
*G06K 9/00* (2006.01)
(52) U.S. Cl. ............... 382/103; 351/209; 345/157; 382/107
(58) Field of Classification Search ............ 382/103, 382/107; 351/209, 210; 345/8, 156, 157
See application file for complete search history.

(56) References Cited

U.S. PATENT DOCUMENTS

| | | | |
|---|---|---|---|
| 4,634,384 A * | 1/1987 | Neves et al. ........... 434/44 |
| 4,973,149 A | 11/1990 | Hutchinson |
| 5,016,282 A * | 5/1991 | Tomono et al. ......... 382/117 |
| 5,231,674 A * | 7/1993 | Cleveland et al. ....... 382/117 |
| 5,325,133 A | 6/1994 | Adachi |
| 5,331,149 A * | 7/1994 | Spitzer et al. .......... 250/221 |
| 5,345,281 A * | 9/1994 | Taboada et al. ........ 351/210 |
| 5,481,622 A * | 1/1996 | Gerhardt et al. ........ 382/103 |

(Continued)

FOREIGN PATENT DOCUMENTS

WO   WO2004/045399   6/2004

OTHER PUBLICATIONS

Yoo, D.Y., et al., "Non-contact eye gaze tracking system by mapping of corneal reflections" IEEE International Conference on Automatic Face and Gesture Recognition (2002).

*Primary Examiner*—Daniel G Mariam
*Assistant Examiner*—Aklilu k Woldemariam
(74) *Attorney, Agent, or Firm*—Stephen J. Schribner; Carol Miernicki Steeg

(57) ABSTRACT

Apparatus and method for eye gaze tracking in human or animal subjects without calibration of cameras, specific measurements of eye geometries or the tracking of a cursor image on a screen by the subject through a known trajectory. One embodiment includes one uncalibrated camera for acquiring video images of the subject's eye(s) and optionally having an on-axis illuminator, and a surface, object, or visual scene with embedded off-axis illuminator markers. The off-axis markers are reflected on the corneal surface of the subject's eyes as glints. The glints indicate the distance between the point of gaze in the surface, object, or visual scene and the corresponding marker on the surface, object, or visual scene.

35 Claims, 16 Drawing Sheets

U.S. PATENT DOCUMENTS

| | | | |
|---|---|---|---|
| 5,638,176 A * | 6/1997 | Hobbs et al. | 356/519 |
| 5,668,622 A | 9/1997 | Charbonnier et al. | |
| 5,898,423 A | 4/1999 | Tognazzini et al. | |
| 5,912,721 A | 6/1999 | Yamaguchi et al. | |
| 6,152,563 A * | 11/2000 | Hutchinson et al. | 351/209 |
| 6,204,828 B1 * | 3/2001 | Amir et al. | 345/7 |
| 6,243,076 B1 | 6/2001 | Hatfield | |
| 6,393,136 B1 * | 5/2002 | Amir et al. | 382/103 |
| 6,578,962 B1 * | 6/2003 | Amir et al. | 351/209 |
| 6,603,491 B2 * | 8/2003 | Lemelson et al. | 715/784 |
| 6,659,611 B2 * | 12/2003 | Amir et al. | 351/210 |
| 6,943,754 B2 * | 9/2005 | Aughey et al. | 345/8 |
| 2003/0123027 A1 | 7/2003 | Amir | |
| 2004/0174496 A1 | 9/2004 | Ji et al. | |
| 2006/0110008 A1 | 5/2006 | Vertegaal et al. | |

* cited by examiner (a)

(b)

(a)

(b)

METHOD AND APPARATUS FOR CALIBRATION-FREE EYE TRACKING USING MULTIPLE GLINTS OR SURFACE REFLECTIONS

RELATED APPLICATIONS

This application claims the benefit of the filing date of U.S. Provisional Patent Application No. 60/519,608, filed on Nov. 14, 2003, and U.S. Provisional Patent Application No. 60/564,615, filed on Apr. 23, 2004. These applications are incorporated herein by reference in their entirety.

FIELD OF THE INVENTION

This invention relates to a method and apparatus for eye gaze tracking in human or animal subjects by analyzing images of the subject's eyes. More specifically, the invention relates to a method and apparatus for eye gaze tracking that does not require calibration of a camera, measurement of eye geometry, or tracking of a cursor, dot pattern, or other image on a screen by the subject through a trajectory. The invention further relates to interactive applications of calibration-free eye gaze tracking.

BACKGROUND OF THE INVENTION

Eye gaze tracking is used in diagnosing and studying physiological and neurological disorders. It is also used as a research tool for understanding various cognitive functions such as vision and reading, in the areas of psychology and neurophysiology, and as a tool for studying effectiveness of marketing and advertising. In such off-line applications, eye gaze fixation data is often analyzed post-hoc, for example, to understand the object of a subject's interest. Eye gaze tracking is also used as an input in interactive applications. For example, in combination with a mouse or keyboard, eye gaze fixations can serve to disambiguate the selection of a target on a computer screen before movement of the mouse is initiated, or before a key is pressed. This allows for the use of a device such as a computer with little or no movement of the limbs; e.g., typing by looking at an on-screen keyboard layout. Further, eye gaze tracking enhances communication with a device through a speech production system, and enables control of a device remotely by looking at the device. Eye gaze tracking can also be used to enhance voice control of multiple devices by disambiguating voice commands. Finally, eye tracking can be used to evaluate effectiveness of visual designs, such as websites and cockpit instrument layouts. The applications of eye gaze tracking continue to grow, as does its importance as input separate from and complementary to the mouse and keyboard.

Wider integration of eye trackers into corporate, professional, and consumer systems requires that eye trackers be easy to use, affordable, and accurate, and less constrained by head and body movements of users. Unfortunately, current eye trackers leave much to be desired, as they are generally expensive, they require users to limit their head movements, and they require calibration, which is typically performed with help of a human operator. As such, current eye trackers are not suitable for applications in public places such as shopping malls or museums or as mass market products. Further, eye trackers with remote optics typically do not work if the user is farther than about 70 cm away from the camera, nor in point of regard tracking on surfaces larger than about 43 cm, thus practically restricting their use to applications such as desktop computers.

FIG. 3 shows the main components of a video-based eye tracking apparatus that utilizes remote optics. An infrared camera 305 is mounted near or below a screen 301, with one or more illuminators 304 placed near the axis 308 of the camera, which produce a bright pupil effect and glint in the eyes of a user, and an image processing facility that allows extraction of the pupil center and glint locations in an eye image. Alternatively, illuminators may be positioned off the optical camera axis, allowing a corneal glint but not a bright pupil. Alternatively, images with alternate on-axis and off-axis illumination are subtracted from one another, to isolate the pupil image. The location of the pupil and the glint in the eyes is typically determined by processing the camera image of the eye through various computer vision techniques.

Most eye tracking techniques require calibration in order to establish the parameters that describe the mapping between the eye coordinates as they appear in the camera image to the visual scene, or display coordinates. Many different calibration techniques exist, most of which involve knowledge of a detailed physiological model of the eye, eyeball radius and corneal curvature, the offset between optical and visual axis, head and eye location, the anterior chamber depth, as measured for a particular user, as well as the distance between the user and the camera, as measured throughout use. Some systems require that the location and angle of the camera is calibrated relative to the visual scene. To calibrate the system, the user is asked to look at a number of features (i.e., calibration points) in the visual scene, typically dots on a screen (for example, reference numerals 503 to 520 on FIG. 5), in sequence. This causes the subject's visual axis to align with the calibration point, which causes the pupil center in the camera image to appear away from the location of the camera glint in the eye, along a gaze vector with angle ρ, denoted reference numeral 523 in FIG. 5. The gaze vector will be different for each calibration point. The resulting set of gaze vectors, for each of which the corresponding point of gaze is known, is used to interpolate a random gaze vector 522, as measured by the eye tracker during operation, in respect of a point of regard 521 between calibration points. This is accomplished through an interpolation function that may include an (estimate of) a number of physiological parameters of the eye, accommodating for head position, screen position and size, and camera location and orientation, to adapt the gaze vector projection into the visual scene to the specific environmental circumstances, including the physiological properties of the subject's eye. This reduces the error in point of gaze projection to an acceptable level, which is typically within 1 degree of the visual angle. System calibration is typically only performed once per user. However, periodic recalibration may be required as environmental circumstances, such as ambient light levels, change.

A clear disadvantage of such prior calibration processes is that they require a continuous and directed effort on behalf of the subject. Such effort may not be available in infant or animal subjects, or in anonymous subjects that are required to use a gaze tracking system unsupervised in public places.

Amir et al. (U.S. Pat. No. 6,659,611, issued Dec. 9, 2003) discusses an approach to calibration in which an invisible test pattern is provided on a display intermittently throughout use. The test pattern may consist of infrared markers embedded in a known geometric formation in the screen. By gauging the warping present in the reflection of markers on the corneal surface, this technique aims to ascertain the mathematical transfer function that maps or interpolates a random gaze vector to arbitrary locations on a visual scene, typically a display. However, this technique has several disadvantages.

Firstly, the mathematical warping function that models the curvature of the eye may be non-trivial. Secondly, the warping function may itself be warped non-linearly with different orientations of the eyeball, as the corneal sphere may not provide the same reflection at all orientations of the eye, requiring continuous measurement of the warping function. Thirdly, the accuracy of this method depends greatly on the accuracy of the underlying model of the eye, since the method itself provides no means of directly associating the location of a glint as reflected on the surface of the cornea, with that of the pupil center or optical axis. Finally, when a single camera is deployed, this technique requires the camera location and angle relative to the head and the screen to be known. Alternatively, it requires the use of a stereoscopic camera system.

U.S. Pat. No. 6,578,962, issued Jun. 17, 2003 to Amir et al., relates to another eye-gaze tracking method which requires two cameras, and requires relative positions and orientations of the cameras and the object being viewed by the subject to be known. This information is known from a one-time, user-dependent calibration of the system. Alternatively, when a single camera is deployed, this technique requires calibration of the radius of curvature of the cornea, and an estimate of the distance of the eye from the camera or the plane of the object being viewed by the subject.

U.S. Patent Application Publication No. 2004/0174496 A1, published on Sep. 9, 2004, relates to an eye gaze tracking method in which gaze is estimated from various calculated eye gaze parameters. This method uses mapping between the camera position and the image plane of the object being viewed, and the camera position must be known.

SUMMARY OF THE INVENTION

The invention provides a method and apparatus for eye gaze tracking in human or animal subjects without calibration of cameras, specific measurements of eye geometries or the tracking of a cursor image on a screen by the subject through a known trajectory. The preferred embodiment includes one uncalibrated camera for acquiring video images of the subject's eye(s) and optionally having an on-axis illuminator, and a surface, object, or visual scene with embedded off-axis illuminator markers. The off-axis markers are reflected on the corneal surface of the subject's eyes as glints. The glints indicate the distance between the point of gaze in the surface, object, or visual scene and the corresponding marker on the surface, object, or visual scene. The marker that causes a glint to appear in the center of the subject's pupil is determined to be located on the line of regard of the subject's eye, and to intersect with the point of gaze.

In a preferred embodiment, point of gaze on the surface, object, or visual scene may be calculated as follows. First, determining which marker glints, as provided by the corneal reflections of the markers, are closest to the center of the pupil in either or both of the subject's eyes. This subset of glints forms a region of interest (ROI). Second, determining the gaze vector (relative angular or cartesian distance to the pupil center) for each of the glints in the ROI. Third, relating each glint in the ROI to the location or identification (ID) of a corresponding marker on the surface, object, or visual scene observed by the eyes. Fourth, interpolating the known locations of each these markers on the surface, object, or visual scene, according to the relative angular distance to the pupil center of their corresponding glints.

In another embodiment, the invention provides a method for eye gaze tracking, comprising: providing an imaging device for acquiring images of at least one of a subject's eyes; providing one or more markers associated with a surface, object, or visual scene for producing corresponding glints or reflections in the subject's eyes; analyzing the images to find said glints and the center of the pupil; and (i) identifying at least one marker corresponding to at least one glint that is within a threshold distance of the pupil center; or (ii) identifying at least two markers corresponding to at least two glints, and calculating a coordinate within the surface, object, or visual scene by interpolating between the location of the two markers on the surface, object, or visual scene according to the relative distance to the center of the pupil of each corresponding glint; wherein the identified marker or interpolated coordinate is indicative of the subject's point of gaze at the surface, object, or visual scene.

The method may further comprise providing an illuminator for producing a glint in the cornea of the subject's eyes, the illuminator being substantially aligned on an optical axis of the imaging device. In further embodiments, the method may further comprise acquiring images of the subject's cornea, the images containing pupils and glints corresponding to at least one on-axis illuminator and at least one off-axis marker. In such embodiments, the at least one off-axis glint may consist of a reflection of at least a portion of the surface, object, or visual scene being viewed by the subject. Further, analyzing may comprise subjecting alternate on-axis and off-axis images to a rolling subtraction algorithm. In one embodiment, for an image sequence A, B, C, D, E, . . . , generated by successive image frames, the rolling subtraction algorithm may comprise subtracting image frames as follows: A-B, C-B, C-D, E-D, . . . .

In another embodiment the method comprises providing an imaging device for acquiring video images of the cornea of at least one of a subject's eyes; providing an illuminator for producing a glint in the cornea of the subject's eyes, the illuminator being substantially aligned on an optical axis of the imaging device; providing one or more markers associated with a visual scene for producing corresponding glints in the cornea of the subject's eyes, the one or more markers being aligned off the optical axis of the imaging device; acquiring alternate on-axis and off-axis video images of the subject's cornea, the video images containing pupils and corresponding on-axis and off-axis glints; analyzing the video images to find one or more glints closest to the center of the subject's pupil; and identifying a marker corresponding to the one or more closest glints; wherein the identified marker is indicative of the subject's point of gaze in the visual scene.

In one embodiment, analyzing comprises subjecting the alternate on-axis and off-axis video images to a rolling subtraction algorithm. The on-axis and off-axis images may be illuminated in an alternating manner, with the illumination of each axis being mutually exclusive, or they may be illuminated by activating the on-axis illuminators every other frame while leaving the off-axis illuminators on constantly. In another embodiment, identifying comprises comparing a position or pattern of one or more markers on the visual scene with a position or pattern of one or more corresponding glints on the cornea, so as to identify a unique marker in the visual scene.

In some embodiments, the method may further comprise uniquely coding each marker in the visual scene, or arranging markers into groups, and uniquely coding each group of markers. In such embodiments, identifying may comprise detecting a code of a marker or group of markers in the cornea, so as to identify a unique marker or group of markers in the visual scene. Uniquely coding markers may comprise using specific wavelengths for individual markers or groups of markers, or uniquely modulating light produced by individual markers or groups of markers.

In a further embodiment, identifying comprises determining a two-dimensional distance metric for the pupil center relative to a coordinate system provided by a position or pattern of the one or more off-axis markers. In another embodiment, identifying comprises: determining, for three markers, three glints closest to the pupil center in the video images; and triangulating between the location of the markers within the visual scene according to the relative contributions of gaze vectors of each of said three glints.

In a preferred embodiment, identifying comprises: determining a region of interest (ROI) containing one or more off-axis glints closest to the center of the pupil; determining a relative angular distance to the pupil center for each off-axis glint in the ROI; relating each off-axis glint in the ROI to the location of a corresponding marker in the visual scene; and interpolating known locations of each said corresponding marker in the visual scene according to the relative angular distance of its glint to the pupil center.

In some embodiments, the invention may be used to obtain information about a subject's visual interest in an object or visual scene. For example, the subject may be a shopper and the visual scene may comprise items on display. In this embodiment, the method may further comprise determining duration of point of gaze on an item; and disclosing information about the item when the duration of point of gaze exceeds a threshold duration. In another example, information may be obtained about the visual interest of subjects for an object on display, such as a product or advertisement, and the information used to determine the cost of displaying that object or advertisement. In other embodiments, the method may comprise determining whether the location of the point of gaze is on the item, and disclosing information about the item to the subject when the location of the gaze is or has been on the item; determining duration of point of gaze on an item, wherein disclosing depends on length of such duration; disclosing information about location and/or duration of point of gaze on an item to a third party; and/or using said information to determine a cost of displaying said item.

Another embodiment comprises identifying uniquely coded markers on objects in a visual scene using the above methods, where the camera is mounted on the head of the subject, pointed at the subject's eye. Alignment of the optical axis of the subject with a uniquely coded marker or markers on an object or group of objects in the visual scene may be carried out by identifying the glint in the subject's eye that is closest to the pupil center. Additionally, moving objects that are tracked by the subject's eye may be identified as being located on the optical axis of the eye by examining the correlated movement of the pupil and the corresponding glint of the marker on the cornea of the eye.

In another embodiment, the visual scene may comprise an electronic device, the method further comprising: determining duration of point of gaze on the electronic device; and initiating speech dialogue with the electronic device when the duration of point of gaze exceeds a threshold duration.

In another embodiment, the visual scene may comprise an electronic device, the method further comprising: determining the duration of point of gaze on the electronic device; and enabling progressively the disclosure of information by the electronic device as the duration of point of gaze increases.

In another embodiment, the visual scene may comprise a video game or a robot, further comprising: determining the point of gaze on an item of the video game or on the robot; and modulating an action of the game item or robot in accordance with the location and/or duration of point of gaze.

In another embodiment, the visual scene may comprise a device or appliance, the method further comprising: determining location and/or duration of point of gaze on the device or appliance; and routing information from a computer, keyboard, or mouse to the device or appliance in accordance with the location and/or duration of point of gaze on the device or appliance.

In another embodiment, the visual scene may comprise a graphical user interface, the method further comprising: determining location and/or duration of point of gaze on a graphical user interface; and controlling placement or arrangement of information on the graphical user interface in accordance with location and/or duration of point of gaze.

In another embodiment, the visual scene may comprise a graphical user interface, the method further comprising: determining point of gaze of a second subject on the graphical user interface; and controlling appearance of information on the graphical user interface at the point of gaze of the second subject. Alternatively, the method may comprise: detecting point of gaze of the subject and one or more additional subjects on the graphical user interface; and modulating appearance of information on the graphical user interface when point of gaze of at least a second subject is detected. In these embodiments, the point of gaze of the first subject and of the second or one or more subjects may overlap, and/or controlling or modulating appearance may comprise positioning a lens or filter on the display according to the point of gaze of the subject and/or the one or more additional subjects, and/or notifying the subject visually and/or aurally of gaze of the one or more additional subjects.

In another embodiment, the visual scene may comprise a graphical user interface, the method further comprising: detecting point of gaze of two or more subjects on the graphical user interface; and controlling appearance of information on the graphical user interface when point of gaze of two or more subjects is detected.

In another embodiment, the visual scene may comprise a noise-cancelling device, the method further comprising: determining point of gaze on the noise-cancelling device; and modulating noise cancelling of the device when in accordance with the point of gaze.

In another embodiment, the visual scene may comprise a communications device, the method further comprising: determining location and/or duration of point of gaze on the communications device; and modulating operation of the communications device in accordance with the location and/or duration of point of gaze.

In another embodiment, the visual scene may comprise a musical instrument or a loudspeaker, the method further comprising: determining location and/or duration of point of gaze on the musical instrument or loudspeaker; and modulating volume of the musical instrument or loudspeaker in accordance with location and/or duration of point of gaze.

According to another aspect of the invention there is provided a method for tracking eye gaze at a moving object, comprising: acquiring video images of at least one of a subject's eyes; detecting movement of at least one glint in the subject's eye; correlating movement of the pupil of the eye with movement of the at least one glint; and identifying the object by (i) detecting a glint associated with the object that appears within a threshold distance from the pupil; or (ii) detecting a glint associated with the object that is moving at the same velocity as the pupil; or (iii) detecting a glint that is moving at the same velocity as the pupil and at the same velocity as the object.

In some embodiments, the method may further comprise providing one or more markers associated with the object, and/or modulating the one or more markers, wherein identifying may further comprise demodulating a glint associated with the one or more markers.

According to another aspect of the invention there is provided an apparatus for carrying out any of the methods set forth above.

According to another aspect of the invention there is provided an apparatus for tracking eye gaze of a subject, comprising an imaging device for acquiring video images of at least one of a subject's eyes; one or more markers associated with a surface, object, or visual scene for producing corresponding glints in the subject's eyes; and an analyzer for analyzing the video images to find said glints and the center of the pupil, and for identifying at least one marker corresponding to at least one glint that is within a threshold distance of the pupil center; and a calculator for calculating a coordinate within a surface by interpolating between the location of the at least one identified marker on the surface according to the relative distance to the center of the pupil of each corresponding glint; wherein the identified marker or interpolated coordinate is indicative of the subject's point of gaze at the surface, object, or visual scene.

In some embodiments, the apparatus may further comprise an illuminator for producing a glint in the subject's eyes, the illuminator being substantially aligned on an optical axis of the imaging device. In a further embodiment, the one or more markers may be aligned off the optical axis of the imaging device.

According to a further embodiment, the apparatus for tracking eye gaze of a subject may comprise: an imaging device for acquiring alternate on-axis and off-axis video images of the cornea and pupil of at least one of a subject's eyes; an illuminator for producing a glint in the cornea of the subject's eyes, the illuminator being substantially aligned on an optical axis of the imaging device; one or more markers associated with a visual scene for producing corresponding glints in the cornea of the subject's eyes, the one or more markers being aligned off the optical axis of the imaging device; and an analyzer for analyzing the video images to find one or more glints closest to the center of the subject's pupil and identifying one or more markers corresponding to the one or more closest glints; wherein the identified one or more markers are indicative of the subject's point of gaze in the visual scene. The on-axis and off-axis images may be illuminated in an alternating manner, with the illumination of each axis being mutually exclusive, or they may be illuminated by activating the on-axis illuminators every other frame while leaving the off-axis illuminators on constantly.

In other embodiments, the imaging device may be adapted to be worn by the user, or the imaging device and a display unit may be adapted to be worn by the user.

According to the invention, a computer may be programmed to execute the method steps described herein. The invention may also be embodied as device or machine component that is used by a digital processing apparatus to execute the method steps described herein. The invention may be realized in a critical machine component that causes a digital processing apparatus to perform the steps herein. Further, the invention may be embodied by a computer program that is executed by a processor within a computer as a series of executable instructions. The instructions may reside in random access memory of a computer or on a hard drive or optical drive of a computer, or the instructions may be stored on a DASD array, magnetic tape, electronic read-only memory, or other appropriate data storage device.

BRIEF DESCRIPTION OF THE DRAWINGS

The invention will now be described, by way of example, with reference to the accompanying drawings, wherein.

DETAILED DESCRIPTION OF THE PREFERRED EMBODIMENTS

Figure 1:
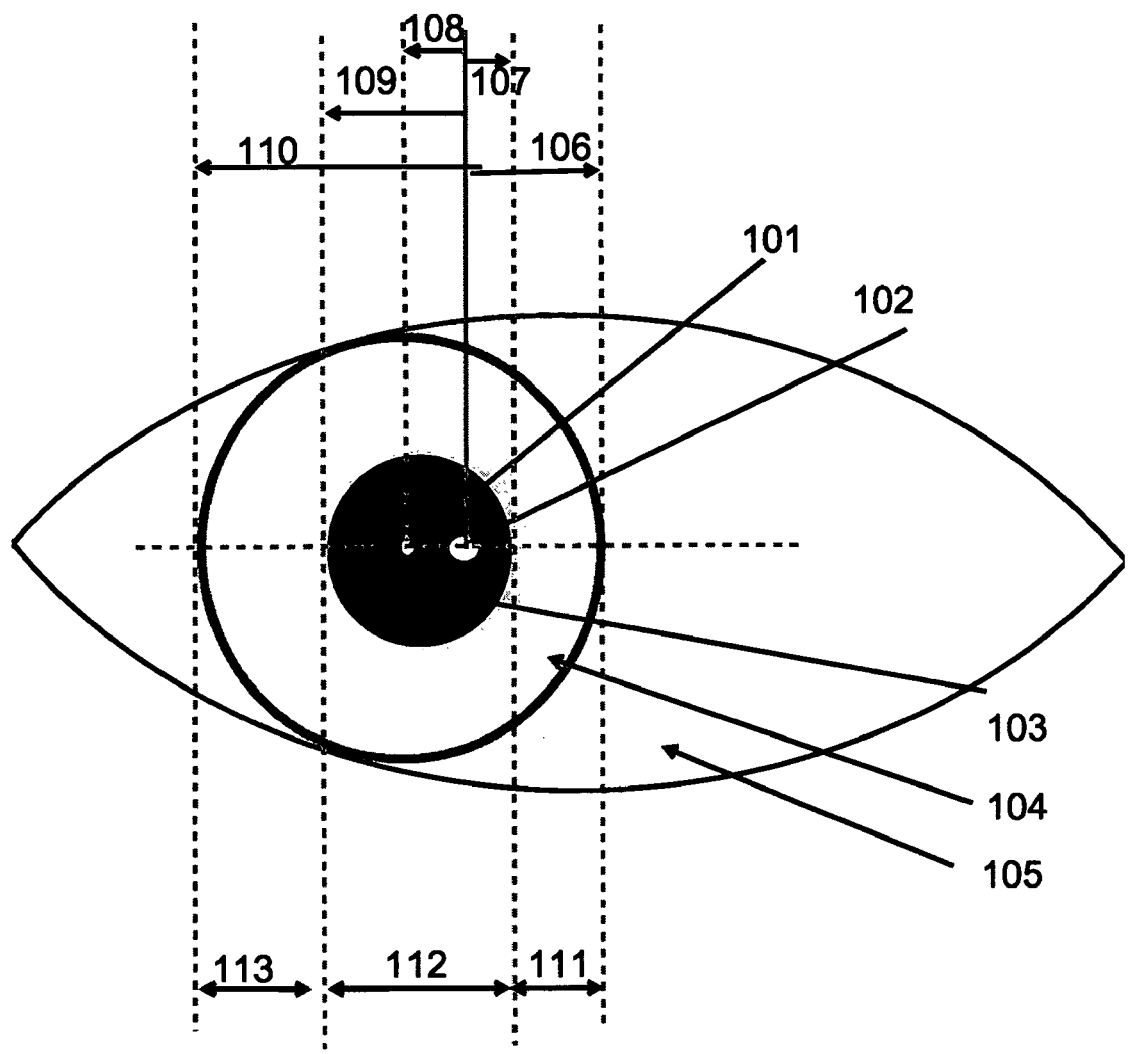
FIG. 1 is a diagram of an eye showing the relationship between various glints produced during eye tracking.

Eye gaze tracking systems based on the bright pupil effect with corneal reflection, as shown in FIG. 1, project light into the eye 105 to determine the angular difference or gaze vector between the center 101 of the pupil 103 and the location of the camera, as indicated by the reflection or glint 102 of the light source in the eye. This glint, also known as the first Purkinje image, serves as a reference point that indicates the camera location irrespective of lateral head movements of the subject. Projecting light into the eye also produces a reflection of light projected through the pupil onto the retina. This retro-reflection makes the pupil appear bright red, and is often observed when using flash photography. This bright pupil effect provides contrast that facilitates differentiation of the pupil from the surrounding iris 104. A typical vision-based eye tracker determines the center of the pupil 101 and the corneal glint 102, as well as the vector 108 between these. The orientation of the eye can subsequently be determined through measuring the distance of the pupil center 101 relative to the glint 102, as provided by the gaze vector 108. The light source that produces glint 102 is typically mounted on or in close proximity to the optical axis of the camera. To avoid distracting the subject, the light source typically operates in the near-infrared area of the spectrum, and the camera is responsive to near-infrared light.

Figure 4:
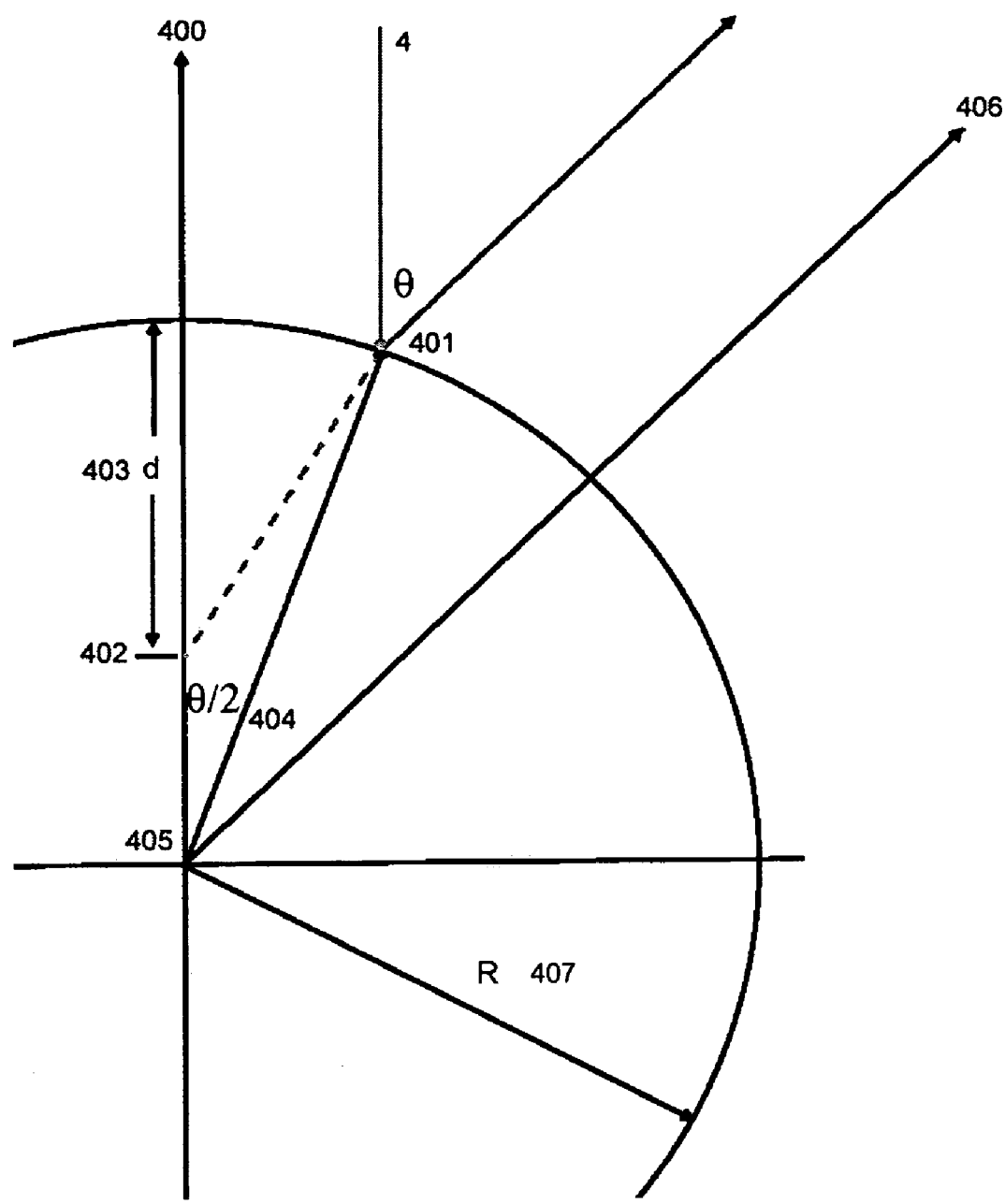
FIG. 4 is a schematic diagram showing that in the corneal sphere, the glint projection from an illuminator as seen from camera location will intersect the gaze vector at distanced from the surface of the sphere.

As shown in FIG. 4, the inventors have recognized that a glint produced by a light source located off axis to the camera also appears at half the angle $\theta$ between the optical axis of the camera 406 and a line 400 that connects that light source with the center of the corneal bulge of the eye 405. Consequently, this glint appears at the pupil center whenever the corresponding off-axis light source is located on the gaze vector 400, substantially irrespective of lateral head movements of the subject.

Figure 2:
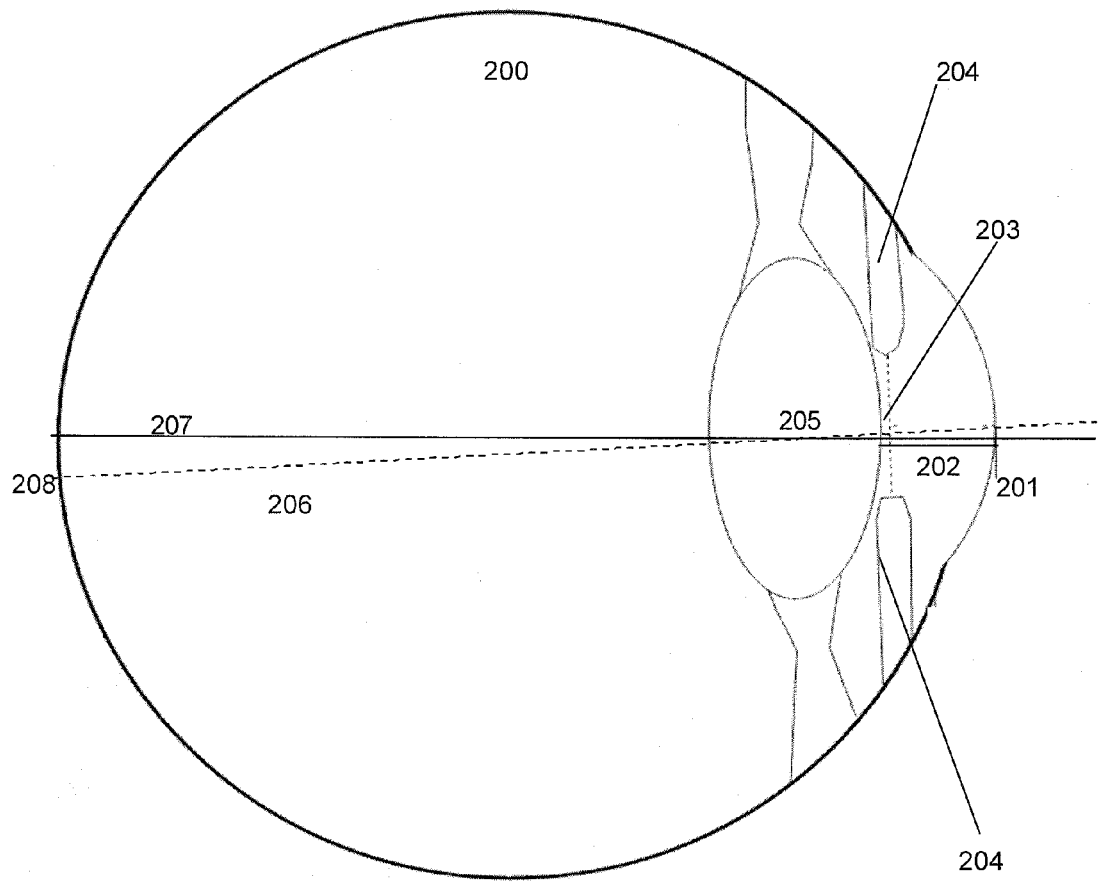
FIG. 2 is a diagram of a lateral cross-section of the eye, adapted from a model in Gullstrand (1955).
Figure 3:
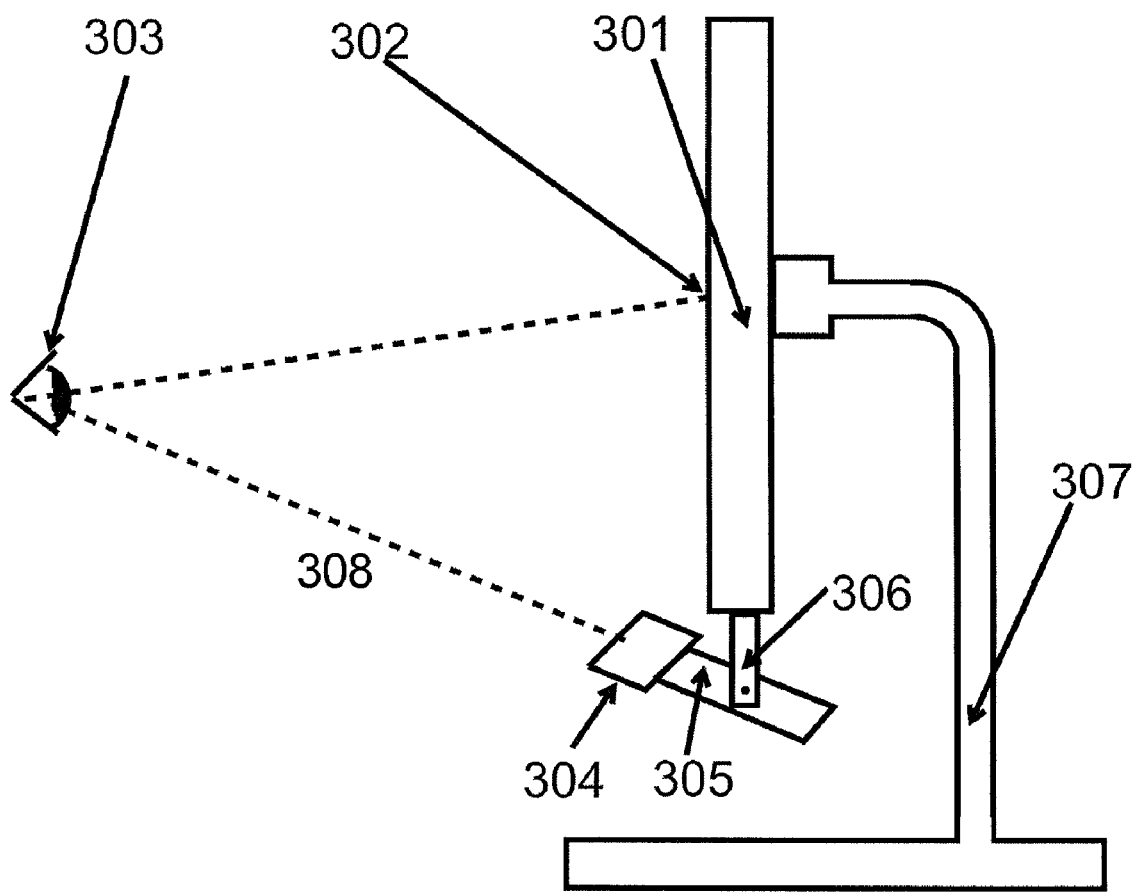
FIG. 3 is a schematic diagram of eye tracking system components (adapted from LC Technologies' Eyegaze System Manual, Fairfax, Va. 1997).

FIG. 2 shows the human eye modelled as two connected spheres, the eye sphere 200 with a mean diameter of 24 mm, and the corneal sphere 201 with a mean diameter of 7.87 mm (standard deviation 0.21 mm) (see Gullstrand 1955). The optical axis of the eye, denoted by reference numeral 207, is defined as the axis or line segment that intersects the centers of rotation of each of the optical elements of the eye. In humans and non-human animals, the distribution of light-sensitive cells in the retina is not uniform. The area in the retina with the best visual acuity is called the fovea centralis 208, which is not located exactly on the optical axis 207 of the eye. Instead, it lies on the visual axis 206, defined as the axis or line segment that connects the fixation point (i.e., the point or "target" being viewed) and the location on the fovea centralis on which the image from that fixation point is seen. The visual and optical axes in normal vision are separated by a mean inward horizontal angle of about 5 degrees of visual angle, with a standard deviation of approximately 1.5 degrees. However, according to Bradley et al. (2003), the offset between the visual axis and optical axis is in practice not so large. This is because the pupil center 203 may be shifted laterally by the iris muscles 204, in such a way that the chief nodal ray (i.e., the ray that enters through the eye's anterior nodal point and exits in a parallel direction from the posterior nodal point) from an object intersects with the fovea centralis 208.

Figure 5:
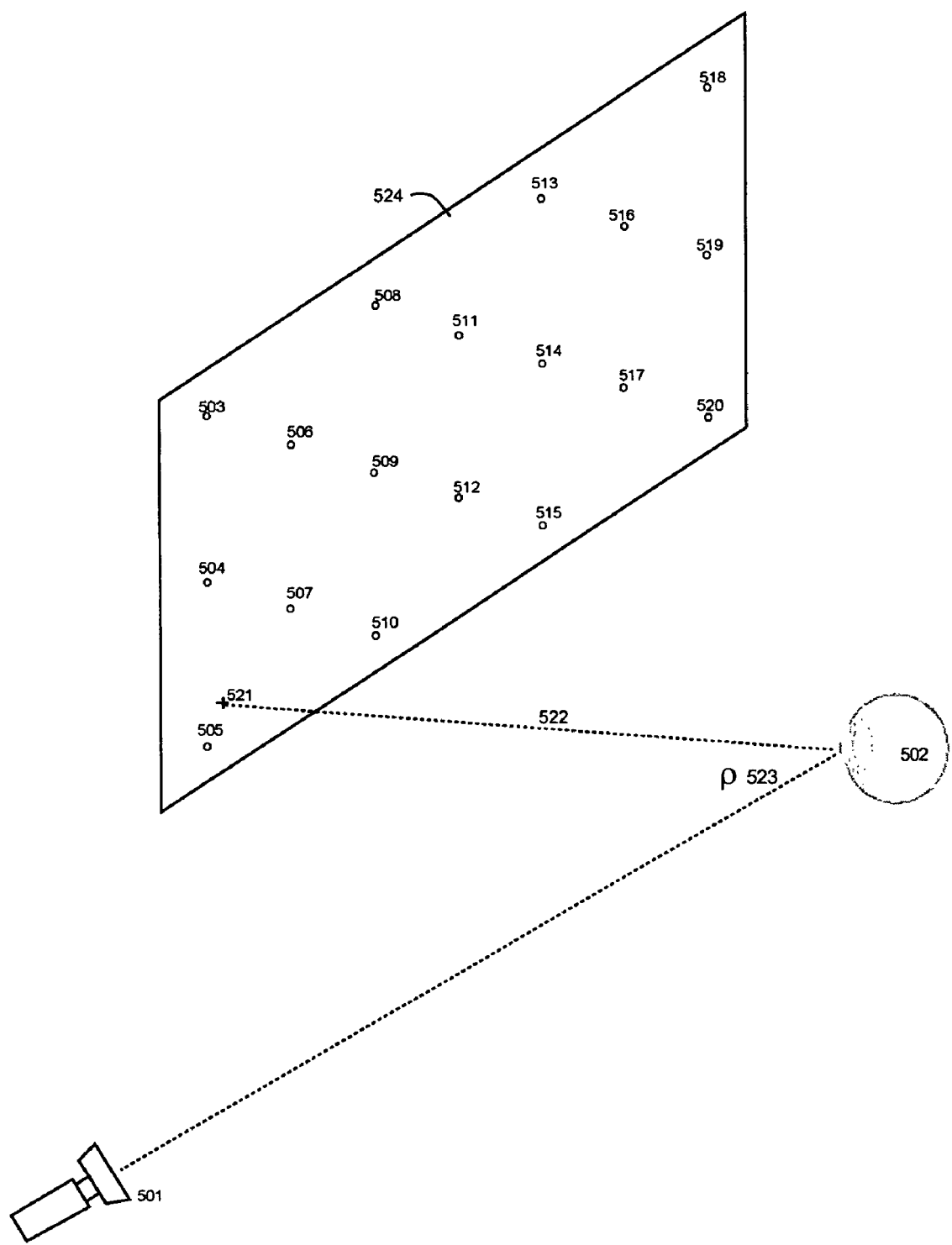
FIG. 5 is a diagram showing projection of an optical axis toward a point of gaze on a surface having multiple markers, from a camera observing the eye at angle ρ from the optical axis. Prior eye tracking systems employ an arrangement in which the markers may be considered as calibration points.

Prior eye tracking systems typically account for the separation between the visual and optical axes through calibration routines. In the present invention, the optical axis of the eye is considered synonymous to the gaze vector. With reference to FIG. 5, the point of gaze 521 is then defined as the intersection between the gaze vector 522 and the observed surface 524. Adjustments for the angular offset of the visual axis from the gaze vector may be made after determination of the gaze vector, through subtraction of a default offset angle. However, our ray tracing models (see FIG. 7) indicate that a separation between the optical and visual axes is not detrimental to our calibration-free eye tracking method for camera angles greater than 20 degrees from the optical axis, and actually improves the accuracy at large angles. This is because the optical and visual axes intersect at the center of the crystalline lens 205 (see FIG. 2), just below the location of the pupil within the eye. A sinusoidal projection of the image in the camera plane further reduces the apparent distance of the visual axis relative to the pupil center location. Although the crystalline lens allows for fine adjustments to the focal length, the cornea performs the bulk of the refraction in the eye. The pupil is offset from the interior surface of the cornea by a distance metric known as the anterior chamber depth (ACD). When this metric is measured from the exterior surface of the cornea 201, it is known as the pseudophakic anterior chamber depth (PACD) 202. The size of the PACD appears to be an evolutionary tradeoff between providing a maximum field of view by refraction of light by the cornea into the pupil, which is greater with larger PACDs, and the refractive power of the crystalline lens 205, which is smaller with larger PACDs. For best results with our calibration-free tracking method, the optimal PACD 202 is at about 4.2 mm, averaged across 90 degrees of visual angle. Indeed, the mean PACD 202 in the emmetropic population (people with 20/20 vision) is about 4.11 mm, with a standard deviation (SD) of 0.24 mm (Rabsilber et al. 2003). The mean diameter of the corneal arc is about 7.87 mm (SD=0.21 mm) (Heijde et al. 2003), with a mean diameter of the eye of about 24 mm (Forrester et al. 1996). A suboptimal PACD may require correction through eye glasses, contact lenses, or laser adjustment of the corneal curve. Such corrective measures will improve the accuracy of our calibration-free tracking to that of subjects with normal vision. It should also be noted that the invention applies equally to an eye having a non-spherical cornea.

DEFINITIONS

As used herein, the following terms are intended to have the meanings as set forth below:

"Illuminator" refers to any active light emitting or passive reflective material, such as, for example, liquid crystal display (LCD), light emitting diode (LED), reflective surface or marker, cathode ray tube (CRT), or laser, irrespective of the emitted or reflected wavelength. Preferably, the illuminator is an infrared LED. The term "on-axis illuminator" refers to an illuminator mounted at or near the imaging device (e.g., camera) lens (see, for example, 1001 in FIG. 10). The term "off-axis illuminator" refers to an illuminator mounted on or near a surface, object, or visual scene on which eye movements are tracked (see, for example, 1000 in FIG. 10).

"Marker" refers to a known point on a surface, object, or visual scene that is used to relate the relative angular orientation of the eye (gaze vector) to a point on the surface. A marker may consist of a portion of the surface, object, or visual scene, or the entire surface, object, or visual scene. A marker may be, for example, an off-axis illuminator. Preferably, the surface, object, or visual scene is not the imaging device. Typically, a mapping is performed using a routine that interpolates the gaze vector between two or more known markers.

"Marker glint" refers to a glint that corresponds to a marker on a surface, such as a planar surface, or on any three-dimensional (3D) or two-dimensional (2D) object, or on a visual scene on which the marker is mounted.

"Interpolation routine" refers to a routine that relates angular gaze vectors relative to a glint to any point on a surface, object, or visual scene, by interpolating between known angular gaze vectors and known markers on the surface, object, or visual scene. Alternatively, a mapping can be provided by ray tracing a model of the eye relative to camera location and angle, and the angle and distance to surface.

"Gaze vector" refers to the angle (e.g., in degrees) between the on-axis glint and the pupil center, as measured in the camera image of the eye. The relative nature of the gaze vector to the on-axis glint (typically indicating the camera location) means it is tolerant to lateral head movement. This is because the corneal surface acts as a convex mirror at angles up to 40 degrees to the on-axis illuminator or camera.

"Optical axis" refers to the axis that contains the centers of rotation of each of the optical elements of the eye.

"Anterior chamber depth" (ACD) refers to the distance along the optical axis between the inside of the cornea and the lens of the eye.

"Pseudophakic anterior chamber depth" (PACD) refers to the distance along the optical axis between the outside of the cornea and the lens of the eye.

"Visual axis" refers to the axis that contains the fixation point and the location on the fovea on which the image is seen.

"Glint" refers to the first Purkinje reflection of an external light source on the cornea of the eye. Typically, when a marker (e.g., an illuminator is reflected in the eye, this reflection relates to a single point, which can be defined mathematically, on the surface, object, or visual scene in/on which the illuminator is embedded or located. In the case of many illuminators, there may be many glints, each relating to a single known location on the surface, object, or visual scene on which the illuminator is located. However, a glint may consist of the reflection of any image, or any part of any image, on or of any surface, object, or visual scene, including a screen image on, for example, a CRT, LCD, plasma, DLP, or any other type of display or projection system used, including natural reflections of surface, object, or visual scene images in the eye of the subject.

"Point of gaze" (POG) refers to the intersection of the gaze vector with the surface, object, or visual scene viewed. This is the coordinate in the coordinate system of the surface, object, or visual scene at which the subject is looking, as determined by an interpolation routine or location of a marker. The POG may be provided in the context of a coordinate system (e.g., two-dimensional), or as an angle.

"Purkinje image" refers to the reflection of light (e.g., from an illuminator) from one of the four major surfaces in the eye: outside cornea (first Purkinje image), inside cornea (second Purkinje image), outside lens (third Purkinje image) and inside lens (fourth Purkinje image). The first Purkinje image corresponds to the glint, as used herein.

"Region of interest" (ROI) refers to the area of the camera image, for example, the area directly surrounding the pupil image, that is selected for processing by a computer vision routine.

"Surface" refers to any surface, including the surface of retinal projection of three-dimensional objects, which may or may not include projection or display on that surface.

"Modulating" refers to changing, such as increasing or decreasing.

Figure 10:
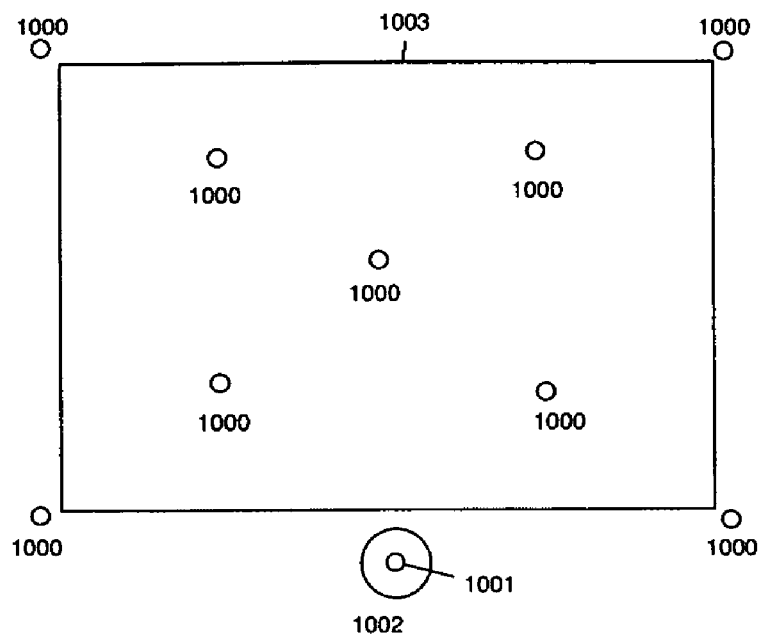
FIGS. 10a and 10b show preferred embodiments of the invention, including a camera with an on-axis illuminator and a surface with 9 markers (a) and 20 markers (b).
Figure 10:
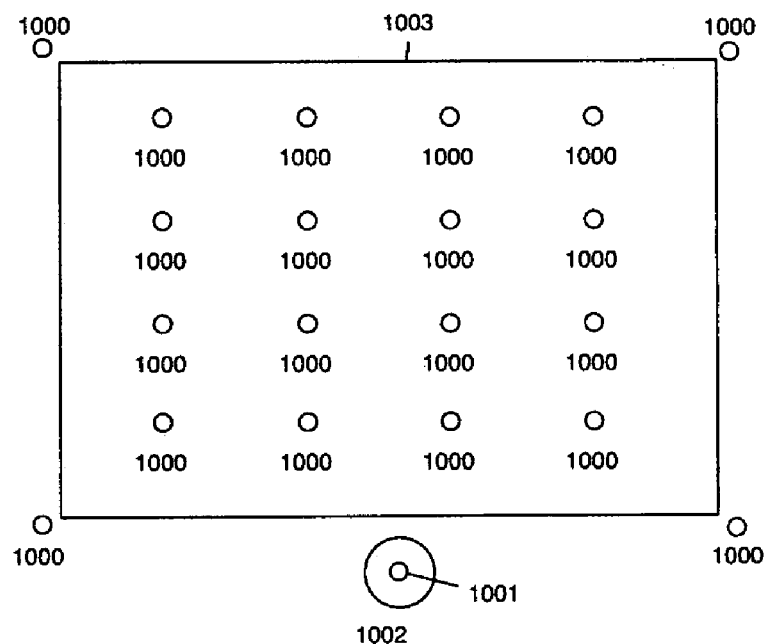
Figure 11:
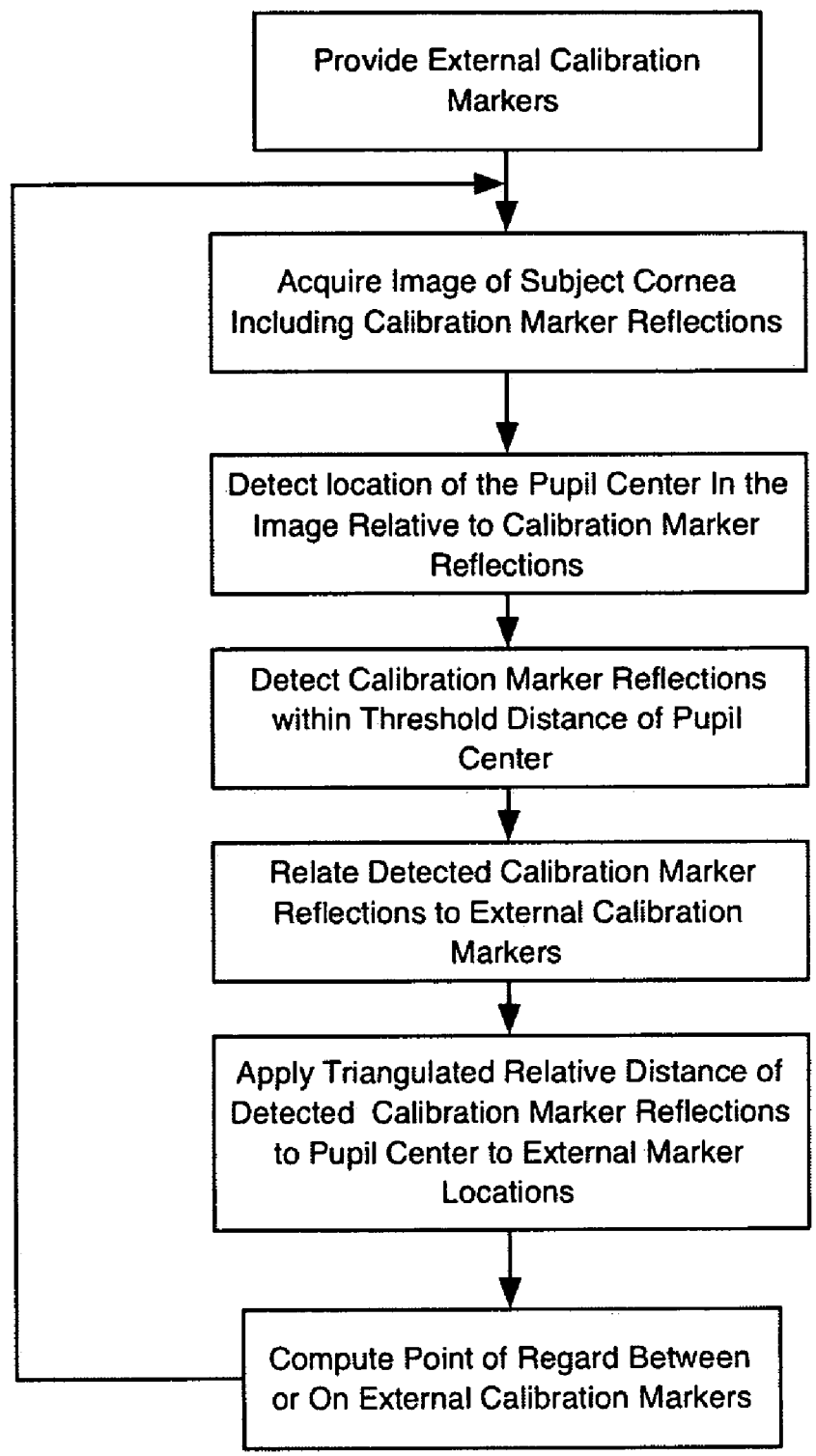
FIG. 11 shows a generalized algorithm for the eye gaze tracking method of the invention.

A preferred embodiment of the invention based on a bright pupil detection or subtraction technique will now be described with reference to FIGS. 5 and 10. A surface 524, in respect of which eye gaze tracking information is sought, is within a subject's field of view. At least one camera 501 captures images of the subject's eye(s) 502. Any number of camera units may be deployed to ensure sufficient coverage of the user's head movement space, or to provide stereo imaging. In the case of the former, subsequent images are stitched together for proper analysis. Although the camera may be an image sensor of any resolution or type sensitive to any (combination of) wavelengths, it is preferably sensitive only to the (near) infrared spectrum of light. The camera(s) may be head-mounted, with the lens pointing at the subject's eye, but is preferably located remotely. Each camera includes an image plane with image coordinate system, a focal center, and an on-axis illuminator (e.g., 1001 on camera 1002 in FIG. 10). The on-axis illuminator's location on/in the camera lens is not critical: for example, a single illuminator may be used, either centered in the lens, or not centered; or several illuminators may circle the lens instead. Note that in other embodiments of the invention that do not employ a bright pupil detection or subtraction technique, the on-axis illuminator 1001 may not be required. The on-axis illuminator may be of any type and emit any (combination of) wavelength. However, to avoid distraction of the subject it preferably emits light at an invisible wavelength, such as (near) infrared. A (near) infrared light emitting diode is an example of a suitable illuminator. At least one off-axis illuminator, or marker, is associated with the surface. For example, in FIG. 5, 18 off-axis illuminators 503 to 520 are associated with the surface 524. For the purpose of this disclosure, the off-axis illuminator(s) will generally be referred to as comprising more than one illuminator; however, it will be appreciated that a single off-axis illuminator may be used. Off-axis illuminators may be embedded in the surface 524, (e.g., where the surface is a computer display or television screen), or mounted on the surface 524. Preferably, the off-axis illuminators also emit light at a non-visible wavelength (e.g., near infrared), so as to avoid distraction of the subject. The camera, with the on-axis illuminator, may be mounted anywhere near the surface 524 at an angle θ (where θ=0 to about 80 degrees) to the center-most illuminator on the surface.

Figure 6:
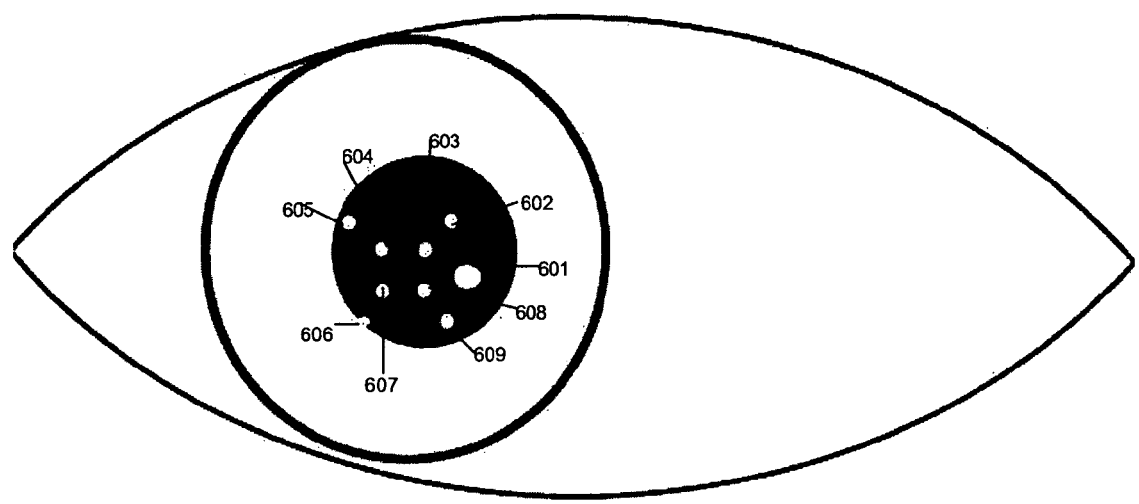
FIG. 6 is a schematic diagram of an eye image with a grid of off-axis marker glints and an on-axis glint.
Figure 9:
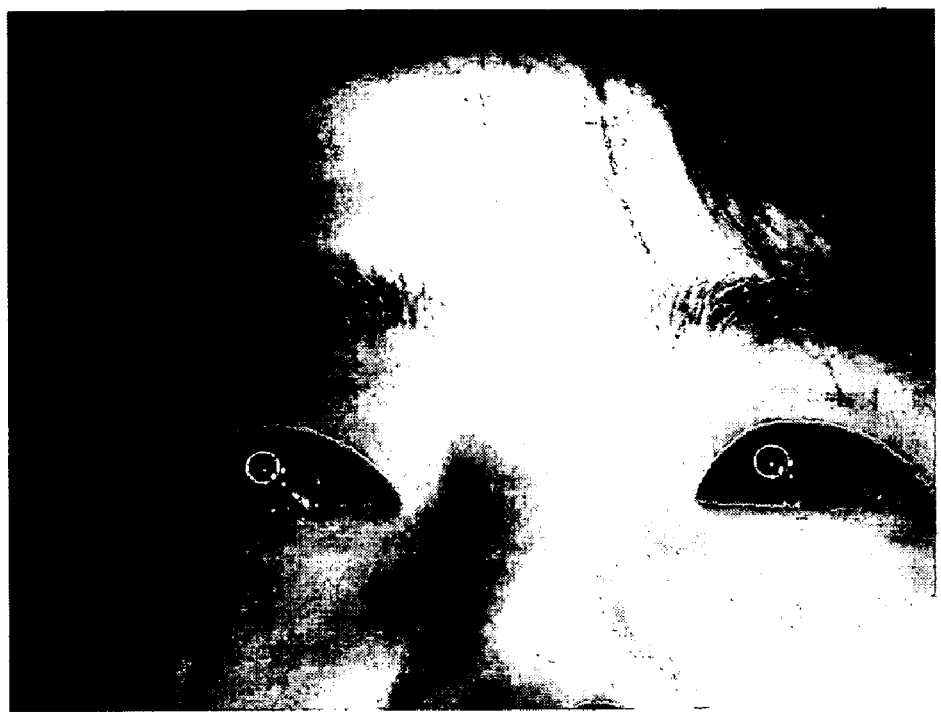
FIGS. 9a and 9b are photographs of a subjects eyes, wherein the circle indicates the detection of a marker glint while user looks at the top right (a) and bottom right (b) infrared markers on a display surface with 5 markers.
Figure 9:
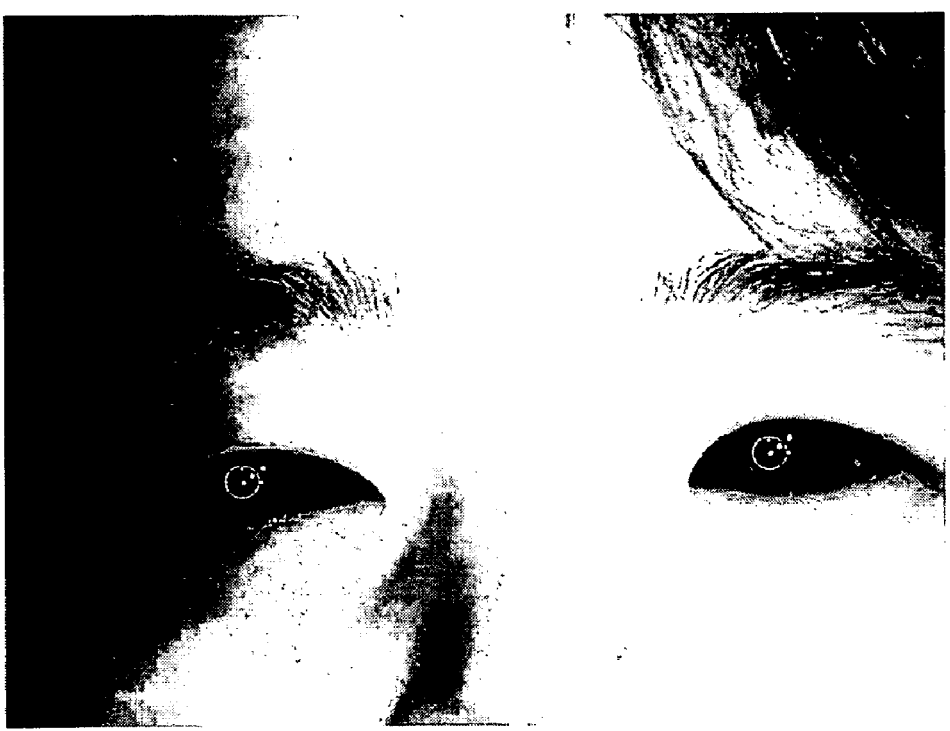

An example of an image of a subject's eyes is shown in FIG. 9 (using five off-axis markers) and schematically in FIG. 6. The image includes image aspects that will be used for determining the gaze vector of the eye as well as its point of gaze, which is the intersection of the gaze vector and the object observed in the visual scene. These image aspects include a glint 601 (FIG. 6) produced by the on-axis light source reflected on the corneal surface at location 0 in eye angular coordinates, thus marking the location of the camera's optical axis in the image of the eye relative to the display surface or objects in the visual scene. Image aspects also include a projection of the pupil image onto the camera image plane, preferably created through retro-reflection as known in the art. The refractive properties of the cornea make this projection appear as a semi-circular ellipsoid even at extreme angles θ of the camera to the optical axis. Techniques are applied for locating the center of the pupil and the center of the on-axis glint, as known in the art.

As noted above, display surfaces on which eye gaze is tracked have embedded therein or mounted thereon off-axis illuminators or markers that function as continuous reference points to the coordinate system of that surface. The surface may or may not involve projection or display of an image or object, but may be referred to as a display surface, display or screen. The markers, which may vary in number but of which there are at least one, may be distributed in any suitable arrangement and density so as to provide the desired resolution of eye gaze tracking, the resolution improving with increasing number of markers. FIGS. 5 and 10 provide examples of marker arrangements on a surface. Thus, markers may be of any distribution, number, wavelength, type, or density, and may include, for example, pixels on a CRT or LCD display, or of actual objects in a visual scene. In a preferred embodiment, the illuminators are LEDs invisibly embedded in the surface, display, or objects in the visual scene that emit (near) infrared light not visible to the subject. In other embodiments markers may be invisibly embedded or attached to any object, passive or dynamic, virtual or real, or in a visual scene, as described below. Since the illuminators will be located off the optical axis of the camera, they do not produce a retro-reflective effect in the pupil image. However, they do produce a glint on the corneal surface of the subject's eye. In the image of the eye observed by the camera, an example of which is shown schematically in FIG. 6, a further image aspect is the grid of markers 602-609 appearing mirrored on the cornea surface as a set of first Purkinje images or glints that are geometrically warped according to the curvature of that cornea.

Referring to FIG. 4, each off-axis illuminator will produce a surface reflection or glint on the cornea, located at an angle of θ/2 in eye angular coordinates within the eye image. As noted previously, θ is the angle between the camera's optical axis 406 and the line segment 400 that connects the marker location with the center of the corneal sphere 405 in the eye. FIG. 4 shows that a glint 401 will intersect the optical axis 400 at distance d 403 from the surface of the cornea. Due to refraction, the projection line of the glint bends when it exits the cornea, intersecting the optical axis at approximately 47% of the distance R 407 from the center of the corneal arc towards the surface of the cornea. If the mean PACD or the average location of the pupil (based on that in the general population) is examined, one observes that d corresponds closely to the mean location of the pupil in the general population at 48% of the distance from the center of the corneal arc R towards the surface.

Figure 7:
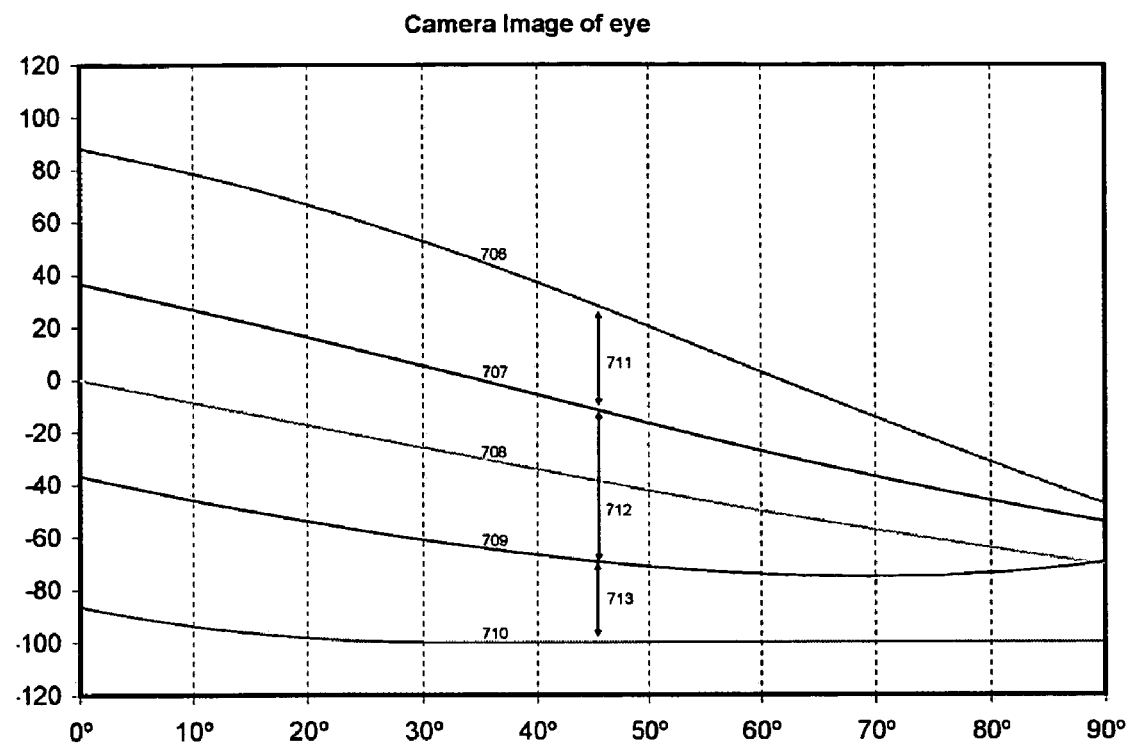
FIG. 7 is a ray trace of the location of a glint 708 from an illuminator located on a surface at the intersection with the eye's optical axis, in pixels from the center of the pupil 712 (with a size of 5 mm), as observed in the image of a camera located at angle θ from the optical axis. Note that the glint stays within 10% of the diameter of the pupil, at up to 80 degrees from the camera.
Figure 8:
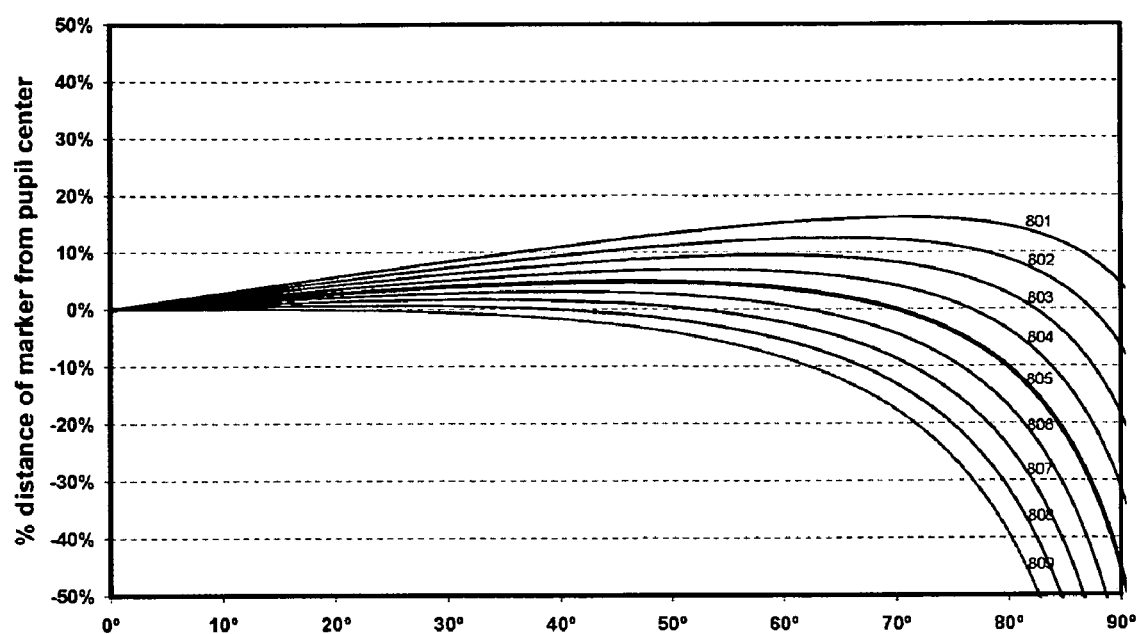
FIG. 8 shows the mean location of the glint of an illuminator on the optical axis 805 in percentage of pupil diameter from the center of the pupil with a mean size of 5 mm, for each 0.5 standard deviation (SD) of pseudophakic anterior chamber depth (PACD) (801-809). Note that the glint will be observed as projected within 10% from the pupil center at up to an 80 degree angle of the camera with the optical axis at a mean PACD (805). At an extreme SD of 2 on either side (801, 809), this remains true at up to 40-60 degrees parallax.

FIG. 7 shows a ray trace model of the location of a glint produced by a marker located on the optical axis of the eye, as it appears projected in the pupil image in the camera (Y axis) for a range of angles θ separating the optical axis of the camera from the optical axis of the eye (X axis). Even at extreme camera angles of 80 degrees to the optical axis of the eye, the center of the pupil image in the camera plane appears located within 10% of the pupil width from the location of the observed marker glint, assuming a mean pupil width of 5 mm (between extremities of 1-8 mm) (Forrester et al. 1996). FIG. 8 shows that this effect appears relatively stable even if standard deviations of the eye physiology for a number of parameters, including PACD, corneal radius and eye diameter, are taken into account.

When the subject's point of regard is at a marker on a surface, this marker can be identified through computer vision as being within a threshold distance to the center of the pupil within the camera image (see FIG. 9). This is true at any distance between the surface and the eye, and up to 80 degrees parallax between the optical axis of the eye and the optical axis of the camera. In a preferred embodiment, the invention identifies the subject's point of regard within the surface by finding the glint(s), for example, 603, 604, and 608 in FIG. 6, that appear(s) closest to the center of the subject's pupil image, and identifying its/their corresponding markers in the surface or visual scene. Note that this process is not limited to three glints, which allows for interpolation between markers. In one embodiment, this is achieved by identifying the mirrored pattern of glints produced by the markers on the cornea, and the relative location of the glints closest to the pupil within this network of glints. Depending on the pattern of markers on the surface, and given a sufficient number of glints from the surface markers in the eye, this uniquely identifies corresponding markers on the surface. In another embodiment, a glint is associated with a marker by identifying a code that uniquely identifies its marker within the visual scene. Coding of illuminators may involve use of specific wavelengths, modulation (e.g., pulse code) of the light energy, or any other known light coding technique, or combination of such techniques. The on-screen point of gaze is provided by determining the center of the pupil, detection of the grid of off-axis illumination points relative to the pupil, and determining the two-dimensional distance metric for the pupil center coordinate relative to the coordinate system provided by the grid of off-axis illumination points.

While typically the grid of off-axis illumination markers—mirrored on the cornea as glints—will be warped, it is straightforward to determine the neighbours in the grid that are nearest to the pupil location. There are known many interpolation functions, any of which can be used to map the pupil coordinate to the surface coordinate. The simplest mapping function is a linear or curvilinear interpolation between the three nearest-neighbour grid points relative to the pupil center. This yields an active interpolation function that maps the location of the pupil to a location between grid points on the screen, with a theoretical accuracy close to that of known commercial vision-based trackers. In a preferred embodiment, the point of gaze is obtained by triangulation between the location of the markers within the visual scene according to the relative contribution of the gaze vector of each of the three glints closest to the pupil center in the camera image. The accuracy of point of gaze measurements may be further improved by modelling, measuring, estimating, and/or calibrating for any number of physiological parameters of the eye, including, for example, but not limited to ACD, pupil size, corneal arc, eye diameter, distance of eye to the camera or surface, vergence between the two eyes, three dimensional head position, relative screen position and size, ambient light conditions, and camera location and angle, to adapt the gaze vector projection into the visual scene to specific and possibly invariant environmental circumstances per subject. For this any method known in the art may be used, including, for example, stereoscopic camera techniques or techniques that incorporate vision of both of the subject's eyes.

Image Processing Algorithm

In a preferred embodiment, to provide active background subtraction, the full-frame retrace synchronization clock of a digital camera with progressive scan is used to switch on or off the on-axis camera illuminator and off-axis illuminators in alternate frames, such that one frame will obtain a bright pupil image with only one glint that indicates the location of the camera unit relative to the markers in the scene. In another preferred embodiment, only the on-axis illuminators are synchronized with the digital camera clock while the off-axis illuminators remain constantly on, such that every other frame will obtain a bright pupil image with only one glint that indicates the location of the camera unit relative to the markers in the scene. In either embodiment, the alternate camera frame will show a dark pupil with a network of multiple glints identifying the location of the off-axis markers relative to the pupil (e.g., FIG. 6). According to techniques known in the art (e.g., Tomono et al., U.S. Pat. No. 5,016,282, issued May 14, 1991), the two images are subtracted to obtain an image that contains only one or several pupils with no background. In this image dark spots inside the pupil indicate the location of the marker glints. A bright spot indicates the location of the camera on-axis illuminator.

According to the invention, a rolling subtraction algorithm is used wherein image sequence A, B, C, D generated by successive camera frames is subtracted as follows: A-B, C-B, C-D, and so on. In a second example, the sequence of frames may be A, B, C, D, E, F, wherein the frames are subtracted as follows: A-B, C-B, C-D, E-D, E-F, . . . , and so on. In a third example, the sequence of frames may be A, B, C, D, E, F, G, H, . . . , wherein the frames are subtracted as follows: A-B, C-B, C-D, E-D, E-F, G-F, G-H, . . . , and so on. It should be apparent that this can be carried out with a minimum of two frames (one on-axis and one off-axis). Further, it should be apparent that in the above examples an even frame in the sequence is always subtracted from an odd frame in the sequence. This guarantees a non-negative result of image subtraction at all times with a single mathematical operation on the images. It also allows for real-time image subtraction with no loss of temporal resolution, and a delay of only a single frame. However, it is also possible to carry out subtraction of odd frames from even frames, or simple subtraction of successive frames.

To correct for dropped frames, a simple computer vision algorithm is used to determine whether the image is illuminated using on-axis or off-axis markers. With suitable filtering and threshold comparisons, only an on-axis image can yield pupil candidates. If the pupil detection algorithm detects the presence of pupil candidates, the input image is classified as an on-axis image; otherwise it is an off-axis image. An additional constraint may be added to improve the classification process. On-axis images will have significantly more non-zero pixels than off-axis images. By counting the number of non-zero pixels after threshold comparisons, the on-axis/off-axis classification is verified for correctness. In a preferred embodiment, pupils and glints are further identified in the image using the algorithms described in FIGS. 11 to 14, and outlined below. Using computer vision threshold comparisons and region-filling algorithms known in the art, the position of the on-axis glint in either the on-axis image or in the subtracted image can be located, providing an active update on the location of the camera relative to the off-axis surface illuminators. This yields a reference point that allows subtraction of head movement from movement of the eyes, and thus head-free operation of the eye gaze tracking technique within certain limits. However, due to the presence of the markers, even without an on-axis marker the camera may be located anywhere within the visual scene, as long as it is within an angle of 0 to approximately 80 degrees of the optical axis of the eye while observing a marker.

Camera location can also be dynamically adjusted while tracking. While this method is tolerant of head movements parallel to the surface, it is also tolerant of head movements perpendicular to the surface, due to the active markers projected continuously on the cornea. As the head moves back, the distance between markers becomes smaller, but the pupil center remains closely aligned with a marker on the optical axis of the eye. This allows for active compensation and proper mapping of the coordinate system, given sufficient resolution in the camera image. These methods work irrespective of camera angle up to about 80 degrees, resolution or type of camera or lens, or wavelength of light used for illumination. In other embodiments, eye gaze tracking may be achieved without the use of the above-described subtraction techniques, using continuous illumination of any or all illuminators, or altogether without the use of markers.

Pupil Detection Algorithm

Figure 12:
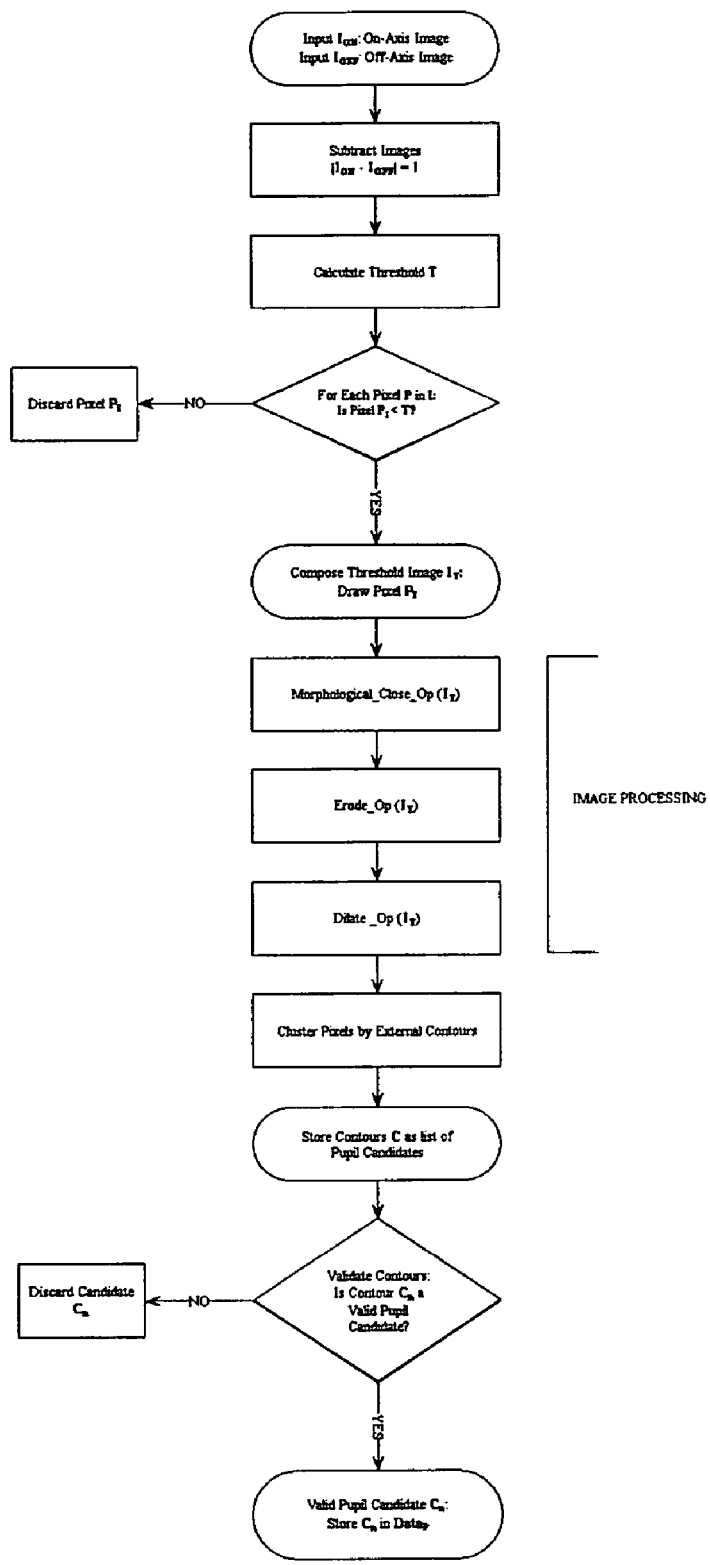
FIG. 12 is an algorithm for pupil detection according to an embodiment of the invention.

The subtracted image provides input for the pupil detection algorithm, an embodiment of which is shown in FIG. 12. In FIG. 12, one or more of the steps marked "Image Processing" may be omitted, or the steps may be carried out in any order, depending on the particular image processing requirements. In the subtracted image, a threshold intensity value T at time t is calculated as follows:

$$T_t = \mu + w\sigma \quad \text{(Equation 1)}$$

where $\mu$ is the mean intensity of the image, $\sigma$ is its standard deviation, and w is a weighting factor. All pixels with an intensity I below this threshold value T are removed. The remaining pixels may be subjected to further post-threshold conditioning by other morphological operations, such as morphological closing/opening, image erosion/dilation, and the like. From the threshold images, the pixels are clustered together and segmented by proximity, forming pupil candidates. This may be accomplished using contour extraction, pixel region growing, edge detection, or any combination of these and/or other image processing techniques. Pattern recognition, or template matching, may also be used to find all shapes that closely resemble that of a pupil (i.e., circular in form). This may be used as is, or in conjunction with the previously-mentioned image processing techniques to further remove noise and false positives.

Glint Detection

Figure 13:
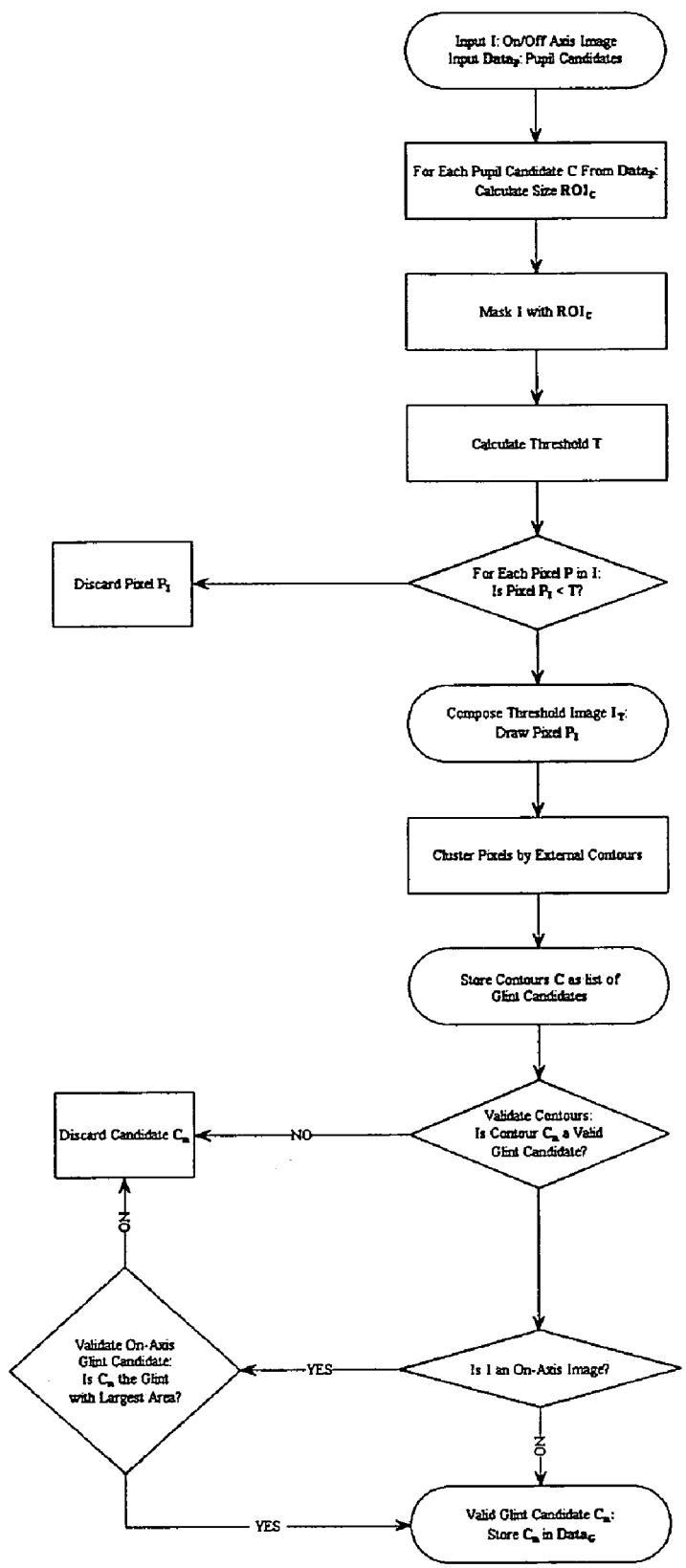
FIG. 13 is an algorithm for marker glint detection according to an embodiment of the invention.

An embodiment of an algorithm for marker glint detection is shown in FIG. 13. By extracting the pupil contours, the exact shape and size of the pupil is detected. To be useful for eye tracking, the glints must be in relatively close proximity to the pupil. Thus glints outside a given region of interest (ROI) surrounding the pupil may be ignored. As shown in FIG. 13, the ROI is dynamically calculated with respect to the size of the pupil. For each pupil, the ROI extends a radius r from the pupil center. To ease calculations, the ROI is calculated as a box extending N pixels around the pupil, where the size of N is calculated relative to pupil size according to radius r. The subtracted image, bounded by an ROI for each pupil found in this image, is analyzed for glints produced by markers using a detection method similar to the above algorithm for detecting the pupil center. Glints produced by on-axis illuminators, when observed in the camera image, amalgamate to form a single large glint. The largest glint in the pupil ROI is defined as the on-axis glint. Alternatively, the on-axis glint may be isolated by analyzing only the image illuminated with the on-axis illuminator, where it appears as the highest intensity glint. The method for detecting the off-axis glints is identical; however, for this it is preferable to use the off-axis image and iterate until all viable candidate glints are found, storing the location of their coordinates within the eye image. To remove noise, a filter may be applied to remove all glint candidates below a threshold intensity or size.

Registration of Glints to Markers

Figure 14:
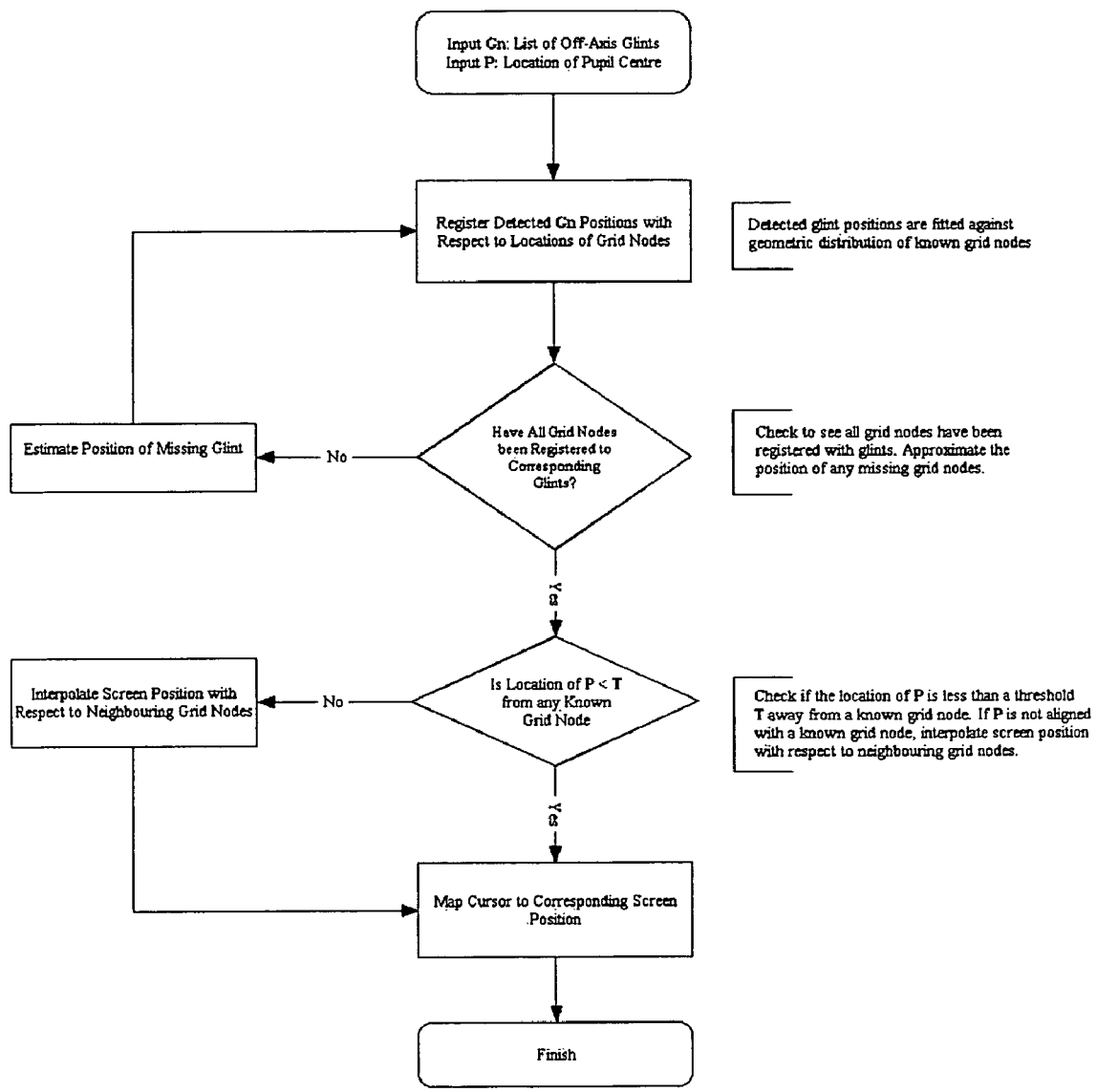
FIG. 14 is an algorithm for mapping glint to marker location according to an embodiment of the invention.

According to a preferred embodiment, for which an exemplary algorithm is shown in FIG. 14, the position of each glint is registered in relation to its neighbouring glints in the network as follows. One method utilizes a pattern recognition approach, using a structured grid-like layout of markers. The grid may be a unique pattern, a repeating pattern, a series of glyphs or pictograms, symmetrical, asymmetrical, or a combination of these layouts. A marker layout is determined beforehand and the detected glint points are matched against this layout in mirror image. When the markers are projected onto the cornea, geometric ratios between markers are used to correctly associate each glint with its position within the layout. With a pattern recognition/template matching approach, using methods known in the art, a complete view of the grid is not required. The position of occluded markers may be inferred from the position of the detected glints. In another embodiment, pulse code modulation (PCM) is used. The Nyquist theorem maintains that a transmitted signal can be accurately reconstructed if the sampling rate of the receivers is at least double that of the transmission rate. Applying this theory in conjunction with PCM, the illumination cycle of individual illuminators, or the marker grid as a whole, may be modulated on or off in subsequent images to transmit a unique binary code according to techniques known in the art. In another embodiment, each illuminator operates at a unique wavelength, and the wavelengths are detected in the camera image.

Tracking Beyond Surfaces and Coding Illuminators

The off-axis illuminators or markers may be mounted, embedded, or projected on any surface or object, and projected upon using any projection system. They may also be mounted on or near a visual display unit such as, but not limited to, an LCD, CRT or plasma screen, at any suitable wavelength. For example, by using between 4 and 15, or more than 15 LCD pixels embedded in a screen as infrared illuminators, markers can be invisibly located in any known LCD display. The more illuminators, the smaller their footprint needs to be to avoid obstructing the view of the pupil, and to obtain better definition of the glints in the cornea. Using this strategy one can theoretically obtain very nearly the same accuracy and precision of eye gaze tracking as is currently possible with commercially available eye gaze tracking systems. By having each illuminator operate at a unique wavelength, or by having them emit a binary tag code through, for example, pulse-code modulation through time, individual illuminators may be identified without any requirement for calibration. By augmenting an object with coded illuminators, one can detect whether the eye is looking at the object, thus identifying the object as well as the interest of the user for the object. For this purpose, a head-mounted eye tracking camera, pointed at the eye of the subject, may be preferred, as it allows for unlimited freedom of movement of the user through three-dimensional space in which objects might be located.

Figure 15:
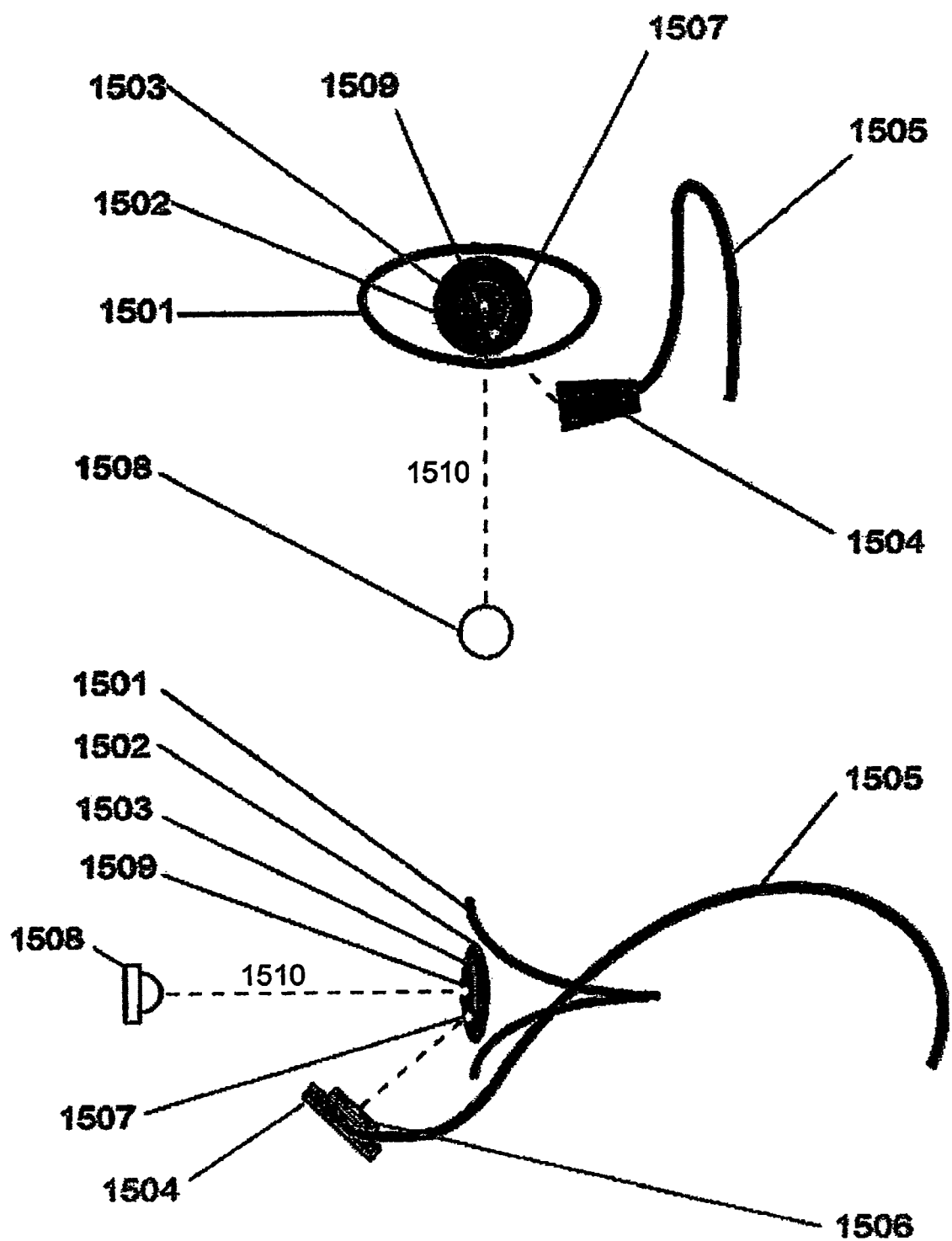
FIG. 15 shows an embodiment of the invention where in a camera with an on-axis illuminator is worn on the head and pointed atone of the subject's eyes. Also shown is the subject looking at an object. The object has a marker that produces a glint near the center of the pupil, with the on-axis glint appearing elsewhere. During movement, the marker glint appears to move with the pupil of the eye as the pupil tracks the object, thus corresponding to the object of interest.

FIG. 15 shows an example of a wearable eye tracker which consists of a small infrared camera 1504 pointed at one of the subject's eyes 1501. The camera 1504 is worn near the eye 1501 within 75 degrees of visual axis from either side of the optical axis of the eye. In one embodiment, the camera is mounted on glasses augmented with an infrared mirror that reflects an image of the eye into the camera unit. In another embodiment it is worn with a flexible band 1505 around the ear. The camera unit has an embedded on-axis illuminator 1506 that provides infrared illumination of the eye. The camera unit may be mounted on a Bluetooth or other wearable headset, for example, as part of a microphone or headphone set. The camera may be either wired or wirelessly connected to a computational device that provides computer vision of the image of the eye obtained through the camera according to the above algorithms. In one embodiment, the camera is embedded in a wearable display unit, and information about eye movements is used to modulate the transparency of the unit, and/or modulate presentation of visual information on the wearable display unit. For example, when the subject is not looking at the display, obstruction of the subject's vision by the display may be minimized by rendering the minimum number of pixels, or by turning the display (semi) transparent. When the subject looks at the display, as indicated by a marker on the display unit, the number of pixels may be increased, for example, by zooming windows on the display, or by fading windows into vision.

Point of gaze on the display may also be used as a means of acknowledging visual notifications. When a visual notification appears on the display unit, it may fade away or shrink if the user does not acknowledge the notification by looking at the display. Conversely, when the user does attend to the display unit, the notification manager may progressively disclose more information about the message, for example by displaying first the subject and sender information and subsequently the body of an incoming email message upon sustained fixations at the display unit.

Tracking of objects in three-dimensional space surrounding the user is performed through computer vision of the eye according to FIG. 15. An infrared marker 1508 is tracked as it moves through the environment. The marker 1508 consists of a set of illuminators such as infra-red LEDs. Circuitry in the marker allows the LEDs to be pulsed with a digital code, for example, a gray code or other form of binary pattern, that serves as a unique identifier for the marker. Alternatively, an object may be identified by wavelength of the light emitted from the marker, or by detecting its natural reflection in the eye (in the latter embodiment, no marking of the object is required). A cell battery may be used to power the circuitry, allowing a marker to be wirelessly embedded in any object, appliance, clothing, etc.

Figure 16:
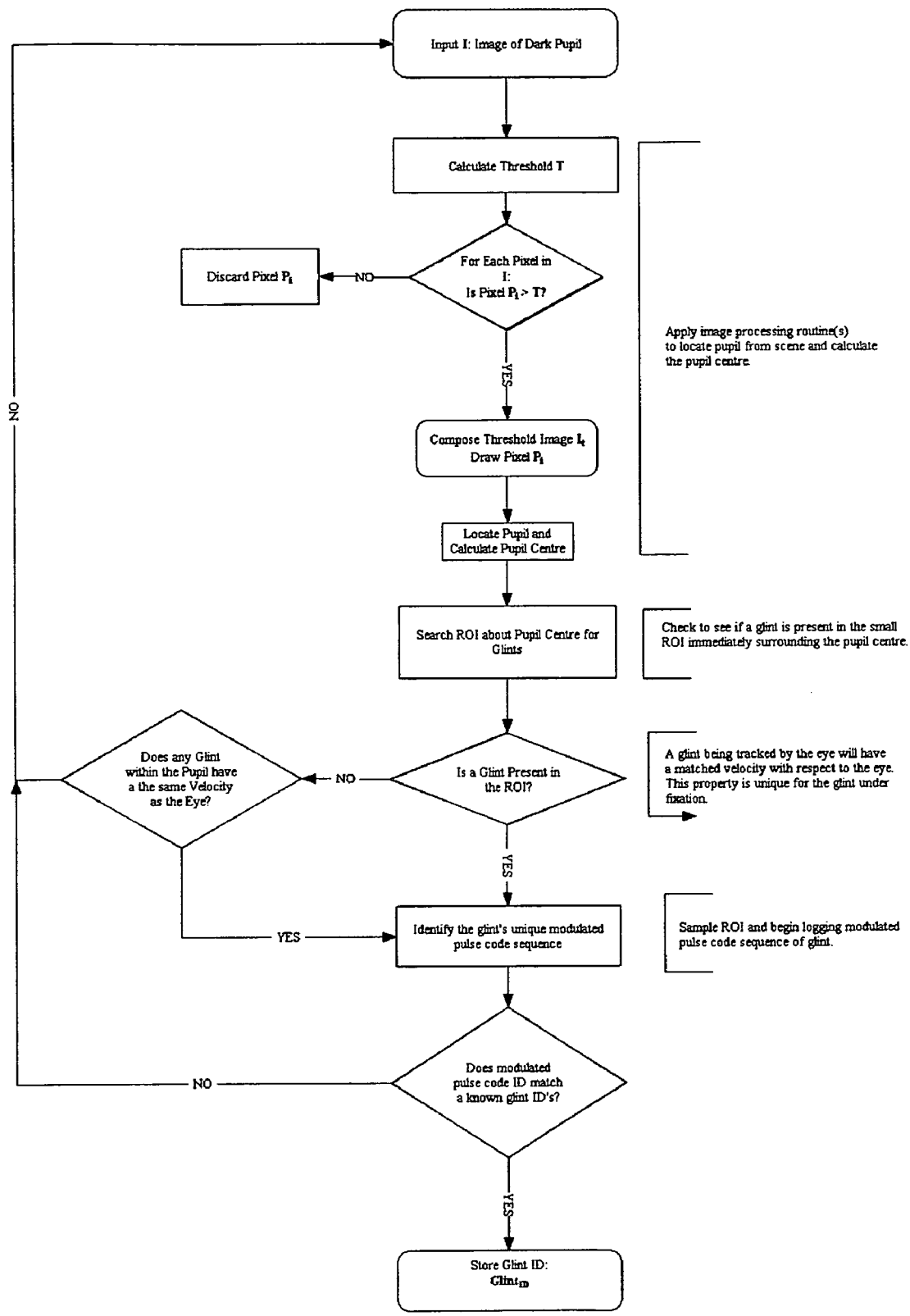
FIG. 16 is an algorithm for identifying markers on objects in 3D space viewed by a subject, according to the embodiment shown in FIG. 15.

An example of a computer vision algorithm for detecting a visual fixation at a moving object is shown in FIG. 16. This algorithm determines which glint, as provided by a marker on an object, is within a set threshold distance from the pupil center. The identity of the object is determined by decoding or demodulating a modulated bit pattern (e.g., pulse code modulation) of the glint in the eye according to the coding scheme used. When marked objects are moving throughout the visual scene, and tracked by the subject's eye, a marker on a current optical axis can be further disambiguated by correlating movement of the eye with that of the object, as it appears through its glint reflection in the eye, which typically appears as the only glint moving at the same velocity as the pupil. The object being viewed is identified by detecting the associated glint that appears within threshold distance from the pupil, or, optionally, the object that is moving with the eye. Glints from marked objects that are not moving with the eye can optionally be discarded as candidates.

Extensions to Natural Light Eye Tracking

While the above-described illumination strategies are limited to the use of active illuminators, any illuminated surface can function as an off-axis image relative to which pupil location can be determined. In particular, when a known image, such as the image on a computer or other display, or a light bulb, is reflected in the pupil, the center of the pupil relative to the visual scene can be detected, as the object that appears reflected near the center of the pupil will be the object on the optical axis of the eye, or the point of gaze. This can be used to achieve natural light eye tracking using displays without infrared illumination, in any real or artificial scene. In one embodiment, identification of the reflection is achieved through a pixel matching algorithm that identifies known objects projected on the cornea near the center of the pupil. In the case of a screen image reflection, a simple autocorrelation function between the screen image and the image mirrored in the cornea can serve this purpose, as long as corneal warping of the mirrored image is taken into account. In effect, any identifiable object on the screen then functions as an active marker. In the case of real-world reflections of real objects, computer vision detection of those objects is required, which may be accomplished using techniques known in the art.

Applications in Human-Computer Interfaces

One application of the invention is to provide eye gaze tracking in small or large surfaces, particularly large displays or projected wall or semi-transparent surfaces, including but not limited to LCD screens, computer screens, SMART boards, tabletop displays, projection screens of any type, plasma displays, televisions, any computing appliance, including phones, PDAs, and the like, and head-mounted and wearable displays and the like, by embedding therein off-axis illuminators. In addition, the invention may be used on any surface, including, for example, walls, tables, furniture, architectural ornaments, billboards, windows, semi-transparent screens, window displays, clothing racks, commercial displays, posters, stands, any commercial or other goods, clothing, car dashboards, car windows, and the like. In addition, and optionally in combination with a wearable unit (where a camera is located on the head aimed at the eye), off-axis illuminators or markers can be located on any object in the external world to identify the user looking at that object. The ID of the object may be provided by modulating the light signal of the illuminator on the object using, for example, a pulse code modulation that provides a binary number, or through identification of the wavelength of the illuminator, or any other method known in the art.

The invention is further described by way of the following non-limiting examples.

Example 1

Applications to Shopping Window Displays

By augmenting any shopping display, such as, for example, computer or television screen-based, projected, static surface, objects, goods (e.g., clothing, furniture), with the invention described herein, eye gaze behavior of subjects (i.e., shoppers) can be tracked for the purpose of registering whether individuals are interested in the goods on display. This can be used for evaluating the design or arrangement of advertisements or arrangements of goods, or for disclosing more information about products or objects to the subject. The following scenario illustrates this application. A clothes rack is augmented with one or more eye tracking cameras, and the clothes or hangers (or any other goods) are augmented with illuminators that have pulse-code modulated ID tags emitted with the light. Cameras detect which item the shopper is interested in by tracking the eye gaze of the shopper, preferably using the methods described herein. When the duration of an eye fixation on an object reaches a threshold, a projection unit displays more information about the goods. Alternatively, in response to a fixation, the subject may be addressed using a recorded message or synthesized computer voice associated with the object of interest, which acts as an automated sales assistant. Alternatively, information about user interest in an article or advertisement may be conveyed to a sales assistant or third party.

Example 2

Progressive Disclosure and Turn-Taking Appliances

Any interactive or non-interactive home appliance can be augmented with the invention, or any other method of eye tracking, and/or with face tracking and/or proximity/body orientation sensing, to determine the availability of users for communications with other people or devices. Subjects may direct the target of speech commands to the appliance, or initiate speech dialogue or other forms of disclosure by the appliance through establishing eye gaze fixation (i.e., looking behaviour) with the appliance. Progressive disclosure of information by the appliance may broaden or otherwise alter the scope of information provided by that appliance, particularly useful for, but not limited to, ambient information appliances (such as an ambient colored light fixture projecting information to the user at low resolution, for example with a particular color that indicates outside temperature, as in the Ambient Orb (Ambient Devices, Inc., 2003) or Auralamp (Mamuji et al., 2003) using techniques known in the art). The appliance detects when user attention, for example, eye gaze, is aimed at the appliance, providing feedback by modulating the energy or color of a light or by producing a sound. To ensure appropriate operation, looking behavior is statistically filtered, for example using a low-pass filter.

Next, the appliance responds to sustained subject eye fixations or orientation towards the appliance by projecting or displaying more detailed graphical or textual information (for example, but not limited to, the temperature and forecast, stock market or news), or by engaging in speech interaction through a speech production system. The latter is referred to as look-to-speak, and can be differentiated from look-to-talk. In look-to-talk, the user identifies the object of his speech command through looking at that object. In look-to-speak, speech production is initiated by the object after sustained looking by the user, for example while that user is silent. Thus, users and (interactive) objects may engage in a smooth exchange of conversation. When user attention is lost for a threshold percentage of time, the appliance initiates a closing sequence of its dialogue or disclosure. As a non-limiting example, a wall or window display augmented with the above technology may be used to advertise information about objects on display, progressively disclosing more information as the user reads the information. The progressive disclosure or turn taking process may be extended to engage multiple appliances or objects simultaneously. The above example is not limited to a light fixture or temperature forecast, but may pertain to any appliance and any content material on any medium.

Example 3

Gaming Applications

Incorporation of the invention, or any other form of eye, face or body tracking technology into a gaming device, portable or otherwise, may provide extra channels of interaction for determining interest in embodied gaming characters. Characters or objects in games can then observe whether they are being looked at by the user and adjust their behavior accordingly, for example by avoiding being seen or by attracting user attention. Alternatively, characters or objects can respond verbally or nonverbally to fixations by the user, engaging the user in verbal, nonverbal, textual, graphical, or other forms of discourse. In the case of speech recognition agents or online human interlocutors, the discourse can be mutual, and the progressive disclosure technique described in Example 2 can be used to structure this discourse. Alternatively, the technology can be used to allow gaming applications to make use of eye gaze information for any control purpose, such as moving on-screen objects with the eyes, or altering story disclosure or screen-play elements according to the viewing behavior of the user. In addition, any of the above may be incorporated into robotic pets, board games, and toys, which may operate interactively at any level.

The following scenario further illustrates this application of the invention. User Alex is playing an online game on his calibration-free eye tracking display. The game is a 3D first-person shooter, and Alex is playing with a team of online friends, represented through 3D avatars. The objective is to defeat the opponent team, which consists entirely of computer-generated actors. An eye tracker on Alex's video display allows the game engine to sense where Alex looks within the visual scene. This information is used to decide when to move or engage enemy actors. A sidebar on the screen shows thumbnail pictures of Alex's team members. Alex can open an audio chat channel with a team member simply by looking, greatly enhancing his ability to coordinate their advance without disrupting manual control of his weapon. However, he has to keep an eye on the screen because enemy forces advance upon detecting he is not paying attention. When Alex turns around, he sees the avatar of his teammate Jeff. Sustained eye contact between Jeff and Alex's avatars opens up an audio chat channel that allows the two to converse in private. When they look back, they notice an opponent advancing in front of them. They aim their weapon by looking at the opponent, eliminating him by pressing a single button on their remote control. Because their hands are no longer overloaded with pointing tasks, Alex's team eventually gains the upper hand, defeating the enemy team.

Example 4

Home Theatre and Advertising Applications

By incorporating the invention into a television display or billboard (e.g., a screen, paper, or interactive display), advertisers can determine what (aspects of) advertisements are viewed by, and hence of interest to, a subject. Advertisers may use this information to focus their message on a particular subject or perceived interest of that subject, or to determine the cost per view of the advertisement, for example, but not limited to, cost per minute of product placements in television shows. For example, this method may be used to determine the amount of visual interest in an object or an advertisement, and that amount of interest used to determine a fee for display of the object or advertisement. The visual interest of a subject looking at the object or advertisement may be determined according to the correlation of the subject's optical axis with the object over a percentage of time that the object is on display. In addition, the method may be used to change the discourse with the television, or any appliance, by channeling user commands to the device or part of the display currently observed. In particular, keyboard or remote control commands can be routed to the appropriate application, window or device by looking at that device or window, or by looking at a screen or object that represents that device or window. In addition, TV content may be altered according to viewing patterns of the user, most notably by incorporating multiple scenarios that are played out according to the viewing behavior and visual interest of the user, for example, by telling a story from the point of view of the most popular character. Alternatively, characters in paintings or other forms of visual display may begin movement or engage in dialogue when receiving fixations from a subject user. Alternatively, viewing behavior may be used to determine what aspects of programs should be recorded, or to stop, mute or pause playback of a content source such as DVD and the like.

Example 5

Control of Notifications

The invention, or any other eye or face tracking system can be used to control the location, size, transparency, shape, or motion of visible notification dialogs on large or small screens according to viewing behavior of the user. In particular, on large screens the technology allows the establishment of peripheral vision boundaries of the user's eyes, ensuring that a window is placed in view. On small screens, notification windows can be placed out of the way of the user's foveal vision, and can be acknowledged and removed after the user has viewed them, as detected according to the invention. In addition, the control of any hidden or visible cursor on a display can be used to communicate attention to underlying applications or systems. In addition, the invention can be applied to the activation and zooming or resizing of focus windows, and to the reorganization of windows on a display, according to the viewing behavior of the user or the movement of the user in front of the display, as measured through the movement of the eyes, head or body. The latter may be accomplished by allowing users to look at the subsequent focus window, after which a key is pressed to activate this window and make it the front window. This may incorporate zooming of the front window according to an elastic tiled windowing algorithm, or fisheye view zoom of the front window using methods known in the art. In addition, the disclosing of attention of others for notes on a public display board, by modulating aspects of size, shape or color of displayed notes, may be accomplished according to the number of times they have been viewed.

Example 6

Gaze-Contingent Display and Privacy Displays

The invention, or any other form of eye tracking, can be used to make the content of a display visible only to the current user, by using eye fixations to position a gaze-contingent blurring lens that is transparent at the fixation point of that user. This results in a screen that can only be read by the current user, and not by any other onlooker. Alternatively, the state of the screen may be altered by, for example, but not limited to, darkening, wiping, or changing its contents. Further, visual or auditory notification may be provided upon detecting more than one pair of eyes looking at the display. This is particularly useful when computing devices are used in public, for private matters. In addition, the invention may be used with any other form of gaze contingent operation where the display is altered according to the viewing behavior of the user. The invention may also be used to modulate transparency of surfaces, for example, but not limited to, cubicle walls, upon orientation or co-orientation of the eyes, face(s), or head(s) of a subject or subjects towards that surface, as measured by eye, face, or body orientation tracking technology. The invention may be used to modulate transparency of a surface as it pertains to an auditory display.

Examples include the modulation of engagement or disengagement of noise-cancelling headphones or the modulation of auditory communications between headphone users upon sensing of eye fixations by one subject at the headset or face of another subject. The invention may also be used to modulate auditory communications between subjects wearing hearing aids or between a subject wearing a hearing aid and another subject or appliance upon sensing of the orientation of the eyes or face of the hearing-disabled subject towards the other subject or appliance. The invention may also be used to modulate the volume of a musical instrument or amplification or speaker system, based on the orientation of the eyes or face of one or more subjects.

Example 7

Vehicle Displays and Dashboards

In accordance with the invention, eye tracking may be incorporated invisibly and without restrictions into vehicles to control dashboard operation, to alter lighting conditions of vehicle illumination or dashboard indicators and instruments, to reduce impact on visual attention. The invention may also be used to alter displays (including projections on windows) according to viewing behavior, for example, to ensure that eyes remain focused on the road, or to direct the destination of speech commands to appliances or objects within or outside the vehicle. In addition, the detection of fatigue, the operation of vehicle navigation systems, entertainment systems, visual display units including video or televisions, the selection of channels on a radio or entertainment system, and the initiation and management of remote conversations may all be carried out using the invention, according to the visual attention of the user.

Example 8

Meeting Support Systems

The invention may be used for sensing attention in remote or same-place meetings, for editing recordings of such meetings, or for the purpose of detecting presence or initiating interactions with remote or co-present attendees, or for communicating attendee attention in order to optimize a turn taking process among several remote attendees.

Example 9

Mobile Media Applications

The invention may be used for sensing user attention towards any mobile or portable computing device to determine when a user is paying attention to the visual information provided on the device. In one embodiment, audiovisual media played on the device may be paused or buffered automatically upon the user looking away from the device. The device continues playing or plays the buffered audiovisual stream whenever the user resumes looking at the device. For example, a mobile device may provide speed reading facilities. The device streams words across a display screen in a timed manner, allowing the user to read without producing fixations. When the user looks away, the stream of words is paused, and when the user looks back at the device, the stream of words continues.

The contents of all cited patents, patent applications, and publications are incorporated herein by reference in their entirety.

While the invention has been described with respect to illustrative embodiments thereof, it will be understood that various changes may be made in the embodiments without departing from the scope of the invention. Accordingly, the described embodiments are to be considered merely exemplary and the invention is not to be limited thereby.

REFERENCES

Ambient Devices, Inc. Ambient Orb. http://www.ambientdevices.com, 2003.

Bradley, A., and Thibos, L. (2003). Modeling Off-axis Vision I: the Optical Effects of Decentering Visual Targets or the Eye's Entrance Pupil. Report, School of Optometry, Indiana University, Bloomington, Ind.

Forrester, J., Dick, A, McMenamin, P. and Lee, W. (1996) *The Eye*. Basic Sciences in Practice, W.B. Saunders, London.

Gullstrand. (1955). Schematic Eye. In *Visual Optics*, H. H. Emsley (Ed), $3^{rd}$ edition, p. 348, Butterworth, Scarborough, Ontario.

Heijde, R. G. L. van der, Dubbelman, M. and Weeber, H. A. (2003). The Shape of the Back Surface of the Cornea. S. Afr. Optom. 62 (3), 132.

Mamuji, A. et al. AuraLamp: Contextual Speech Recognition in an Eye Contact Sensing Light Appliance. In Extended Abstracts of Ubicomp'03, Seattle, 2003.

Olsen T., Olesen H., Thim K., Corydon L. (1992) Prediction of Pseudophakic Anterior Chamber Depth with the Newer IOL Calculation Formulas. J. Cataract Refract. Surg., 1992 18: 280-285.

Rabsilber T. M., Becker K. A., Frisch I. B., Auffarth G. U. (2003). Anterior Chamber Depth in Relation to Refractive Status Measured with the Orbscan II Topography System. J. Cataract Refract. Surg., 2003 Nov. 29(11): 2115-21.

The invention claimed is:

1. A method for determining a subject's point of gaze, comprising:
    providing an imaging device for acquiring images of at least one of a subject's eyes;
    providing one or more markers associated with a surface, object, or objects in a visual scene for producing one or more corresponding glints or reflections in the subject's eyes;
    analyzing the images to find glints that are within a threshold distance of the pupil center;
    identifying, from the glints that are within a threshold distance of the pupil center, a glint that is closest to the pupil center; and
    identifying the marker corresponding to the glint that is closest to the pupil center;
    wherein the one or more markers are off an optical axis of the imaging device; and
    wherein the identified marker is indicative of the subject's point of gaze at the surface, object, or objects in the visual scene.

2. The method of claim 1, further comprising providing an illuminator for producing a glint in the subject's eyes, the illuminator being substantially aligned on an optical axis of the imaging device.

3. The method of claim 2, further comprising:
    acquiring images of the subject's eyes, the images containing pupils and glints corresponding to at least one on-axis illuminator and at least one off-axis marker.

4. The method of claim 3, wherein the at least one off-axis glint consists of a reflection of at least a portion of the surface, object, or objects in the visual scene being viewed by the subject.

5. The method of claim 3, wherein:
acquiring images comprises acquiring alternate on-axis and off-axis images of at least one eye; and
analyzing comprises subjecting alternate on-axis and off-axis images to a rolling subtraction algorithm.

6. The method of claim 5, wherein, for an image sequence A, B, C, D, E, ..., generated by successive image frames, the rolling subtraction algorithm comprises subtracting image frames as follows: A-B, C-B, C-D, E-D, ....

7. The method of claim 1, wherein identifying a marker comprises comparing a position or pattern of one or more markers on the surface, object, or objects in the visual scene with a position or pattern of one or more corresponding glints, so that the marker is identified.

8. The method of claim 1, further comprising uniquely coding each marker in the visual scene.

9. The method of claim 1, further comprising arranging markers into groups, and uniquely coding each group of markers.

10. The method of claim 8, wherein identifying a marker comprises detecting a code of a marker or group of markers, so that the marker is identified.

11. The method of claim 8, wherein uniquely coding markers comprises using specific wavelengths for individual markers or groups of markers.

12. The method of claim 8, wherein uniquely coding markers comprises uniquely modulating light produced by individual markers or groups of markers.

13. Apparatus for determining a subject's point of gaze, comprising:
an imaging device for acquiring images of at least one of a subject's eyes;
one or more markers associated with a surface, object, or objects in a visual scene for producing one or more corresponding glints in the subject's eyes; and
a means for analyzing the images to find glints that are within a threshold distance of the pupil center; for identifying, from the glints that are within a threshold distance of the pupil center, the glint that is closest to the pupil center; and for identifying the marker corresponding to the glint that is closest to the pupil center;
wherein the one or more markers are off an optical axis of the imaging device; and
wherein the identified marker is indicative of the subject's point of gaze at the surface, object, or objects in the visual scene.

14. The apparatus of claim 13, further comprising an illuminator for producing a glint in the subject's eyes, the illuminator being substantially aligned on an optical axis of the imaging device.

15. The apparatus of claim 13, wherein the imaging device is adapted to be worn by the user.

16. The apparatus of claim 15, further comprising a display unit to be worn by the user.

17. The method of claim 1, wherein the subject is a shopper and the surface, object, or objects in the visual scene comprises at least one item on display.

18. The method of claim 17, further comprising:
determining whether location of the point of gaze is on the item; and
disclosing information about the item to the subject when the location of the point of gaze is or has been on the item.

19. The method of claim 18, wherein determining comprises determining duration of point of gaze on the item; and disclosing depends on length of such duration.

20. The method of claim 18, further comprising disclosing information about location, duration, or location and duration of point of gaze on the item to a third party.

21. The method of claim 20, wherein the information is used to determine a cost of displaying the item.

22. The method of claim 1, wherein the visual scene comprises an electronic device, the method further comprising:
determining location, determining duration, or determining location and duration of point of gaze on the electronic device; and
initiating speech dialogue with the electronic device in accordance with the location, duration, or location and duration of point of gaze.

23. The method of claim 1, wherein the one visual scene comprises an electronic device, the method further comprising:
determining location, determining duration, or determining location and duration of point of gaze on the electronic device;
wherein the electronic device progressively discloses information in accordance with the location, duration, or location and duration of point of gaze.

24. The method of claim 1, wherein the visual scene comprises a video game or a robot, the method further comprising:
determining location, determining duration, or determining location and duration of point of gaze on the video game or on the robot; and
modulating an action of the game or robot in accordance with the location, duration, or location and duration of point of gaze.

25. The method of claim 1, wherein the visual scene comprises a device or appliance, the method further comprising:
determining location, determining duration, or determining location and duration of point of gaze on the device or appliance; and
routing information from a computer, or input device such as keyboard, mouse or remote control to the device or appliance in accordance with the location, duration, or location and duration of point of gaze.

26. The method of claim 1, wherein the visual scene comprises a graphical user interlace, the method further comprising:
determining duration of point of gaze on a location on the graphical user interface; and
controlling placement or arrangement of information on the graphical user interface in accordance with the duration of point of gaze on the location.

27. The method of claim 1, wherein the visual scene comprises a graphical user interface, the method further comprising:
detecting point of gaze of the subject and one or more additional subjects on the graphical user interface; and
modulating appearance of information on the graphical user interface when point of gaze of at least a second subject is detected.

28. The method of claim 27, wherein respective points of gaze of the subject and of the one or more additional subjects overlap.

29. The method of claim 27, wherein modulating appearance comprises positioning a lens or filter on the display according to the point(s) of gaze of the subject and/or the one or more additional subjects.

30. The method of claim 27, wherein modulating appearance comprises notifying the subject visually and/or aurally of detection of eyes or point of gaze of the one or more additional subjects.

31. The method of claim 1, wherein the visual scene comprises a noise-cancelling device, the method further comprising:
- determining point of gaze on the noise-cancelling device; and
- modulating noise cancelling by the device in accordance with the point of gaze.

32. The method of claim 1, wherein the visual scene comprises a communications device, the method further comprising:
- determining location, determining duration, or determining location and duration of point of gaze on the communications device; and
- modulating operation of the communications device in accordance with the location, duration, or location and duration of point of gaze.

33. The method of claim 1, wherein the visual scene comprises a device selected from a musical instrument, a loudspeaker, and a hearing aid, the method further comprising:
- determining location, determining duration, or determining location and duration of point of gaze on the device; and
- modulating volume of the device in accordance with the location, duration, or location and duration of point of gaze.

34. The method of claim 1, including providing two or more markers associated with the surface, object, or objects in the visual scene for producing two or more corresponding glints or reflections in the subject's eyes.

35. The apparatus of claim 13, including two or more markers associated with the surface, object, or objects in the visual scene for producing two or more corresponding glints in the subject's eyes.

* * * * *

UNITED STATES PATENT AND TRADEMARK OFFICE
CERTIFICATE OF CORRECTION

| | |
|---|---|
| PATENT NO. | : 7,809,160 B2 |
| APPLICATION NO. | : 10/987299 |
| DATED | : October 5, 2010 |
| INVENTOR(S) | : Roel Vertegaal et al. |

It is certified that error appears in the above-identified patent and that said Letters Patent is hereby corrected as shown below:

Column 26, Claim 23, Line 14: delete the word "one".

Signed and Sealed this
Seventeenth Day of May, 2011

David J. Kappos
*Director of the United States Patent and Trademark Office*